United States Patent [19]

Onodera et al.

[11] 4,277,553
[45] Jul. 7, 1981

[54] LIGHT-SENSITIVE COLOR PHOTOGRAPHIC MATERIAL

[75] Inventors: Kaoru Onodera; Noboru Mizukura; Ryuichiro Kobayashi, all of Hino, Japan

[73] Assignee: Konishiroku Photo Industry Co., Ltd., Tokyo, Japan

[21] Appl. No.: 76,543

[22] Filed: Sep. 19, 1979

[30] Foreign Application Priority Data

Sep. 20, 1978 [JP] Japan .............................. 53-115454

[51] Int. Cl.$^3$ .......................... G03C 5/54; G03C 1/10
[52] U.S. Cl. .................................. 430/216; 430/223; 430/551; 430/559
[58] Field of Search ............... 430/551, 372, 216, 223, 430/559

[56] References Cited

U.S. PATENT DOCUMENTS

| | | | |
|---|---|---|---|
| 2,403,721 | 7/1946 | Jelley et al. | 430/551 |
| 2,675,314 | 4/1954 | Vittum et al. | 430/372 |
| 2,728,659 | 12/1955 | Loria et al. | 430/551 |
| 3,801,322 | 4/1974 | Shirasu et al. | 430/372 |
| 3,930,866 | 1/1976 | Oishi et al. | 430/551 |
| 4,113,495 | 9/1978 | Shishido et al. | 430/551 |

FOREIGN PATENT DOCUMENTS 2839434  3/1979  Fed. Rep. of Germany ........... 430/551

*Primary Examiner*—J. Travis Brown
*Attorney, Agent, or Firm*—Bierman & Bierman

[57] ABSTRACT

A silver halide emulsion containing an image dye-forming substance and a hydroquinone compound containing at least one electron attracting group as a color fog inhibiting agent.

18 Claims, No Drawings

LIGHT-SENSITIVE COLOR PHOTOGRAPHIC MATERIAL

This invention relates to a light-sensitive color photographic material having improved photographic properties, and more particularly to a light-sensitive silver halide color photographic material containing a hydroquinone compound as a color fog inhibiting agent.

As a process for obtaining a color image by the reaction of a image dye forming substance associated with a light-sensitive silver halide emulsion with an oxidation product of a developing agent produced as the result of development of exposed silver halide, a variety of processes are well known. In these processes, when the image dye forming substance is a coupling substance such as a color forming coupler which is used in an ordinary color developing process or a diffusible dye releasing coupler (hereinafter referred to as DDR coupler), the developing agent is a color developing agent such as p-phenylenediamine, type compound p-aminophenol type compound or a derivative thereof. Further, when the image dye forming substance is one which can cause a redox reaction with the oxidation product of a developing agent, such as a dye releasing redox compound (hereinafter referred to as DRR compound), black-and-white developing agent such as a hydroquinone or 3-pyrazolidone type developing agent may also be used in addition to the aforementioned color developing agents.

In practicing these processes, practicians are often encountered with difficult problems of color fog or stain. These phenomena are observed because a developing agent is often oxidized independently of the developing reaction with an exposed silver halide and the oxidation product of the developing agent immediately reacts with a image dye forming substance. Actually a dye image must be formed corresponding to the development of the exposed silver halide and thus formed oxidation product of a developing agent should react with a image dye forming substance to give an image dye. In a color diffusion transfer process, such image dye may be formed in an image-receiving layer.

This undesirable oxidation of the developing agent, which is considered to occur either because of the action of air or some other reactions which is independent of the silver image forming reaction, results in the occurrence of color fog or color stain in the light-sensitive material. Such color fog or color stain cannot satisfactorily be prevented by a stabilizing method usually applied to silver halide emulsion.

On the other hand, it is important for a light-sensitive photographic material for a multi-color image forming process to have less color fog or stain to give satisfactory color separation. The image dye forming substance should yield a dye by reacting with the oxidation product of a developing agent produced corresponding to the development of exposed silver halide grains. However, since the oxidation product of a developing agent is generally diffusible, it can diffuse into a adjacent hydrophilic layer and cause an undesirable dye forming reaction. These phenomena result in a deterioration of color separation and color reproduction such as color mixing which is often observed in a multi-color photography. In particular, such phenomena give rise to a serious problem when a rapid development such as high temperature development or development using a high alkali developing solution is employed or when a developing agent as 1-phenyl-3-pyrazolidone type, the oxidation product of which is, because of its stability and diffusibility, able to effect the dye image formation reaction and has an inclination to effect said reaction in other layers, is used.

With a view to controlling color fog or color stain and preventing deterioration of color reproduction, it has been known in the art to use a hydroquinone compound.

For example, use of an alkyl hydroquinone is described in Japanese Patent Publication No. 50-21249/1975 and No. 50-23813/1975, and Japanese Patent Publications for Open to Public Inspection (hereinafter referred to as Japanese OPI Patent Publication) No. 49-106329/1974 and No. 49-129535/1974; in U.S. Pat. Nos. 2,336,327, 2,360,290, 2,403,721, 2,544,640, 2,732,300, 2,782,659, 2,937,086, 3,637,393 and 3,700,453 and British Pat. No. 557,750; and use of an aryl hydroquinone is described in U.S. Pat. No. 2,418,613. Further, U.S. Pat. Nos. 2,675,314, 2,701,197, 2,704,713, 2,710,801, 2,816,028 and 3,236,893 and British Pat. Nos. 891,158 and 1,156,167 and Japanese OPI Patent Publication No. 53-32034/1978 disclose use of other hydroquinone compounds. Use of these hydroquinone compounds in the combination of two or more of them is also described in Japanese OPI Patent Publications No. 50-156438/1975 and 51-6024/1976 and in Research Disclosure, 152, 19.

However, these hydroquinone compounds have such drawbacks which are disadvantageous to a color photographic material that some of them can be prepared only by a complicated process; they often cause undesirable side-reaction due to unsatisfactory non-diffusibility; they cannot achieve satisfactory inhibition of color stain or prevention of color mixing because their inherent ability is rather poor; they must be used in a large amount; they are liable to crystallize while they are used, for example, before, during or after coating; they have harmful physical or chemical effects on coated layers; or they form a colored product due to a oxidation reaction caused during the coating procedure or processing procedure.

According to our research, these drawbacks caused by the known hydroquinone compounds mainly result from depending on the degree of their ability to make the oxidation product of the developing agent inactive by reacting with said oxidation product (this ability will hereinafter be referred to as a scavenging ability).

Thus, by the use of such hydroquinone compounds that could satisfactorily inhibit color fog or color mixing only in a small amount, the afore-mentioned drawbacks, would be removed.

Therefore, recently, in the field of manufacturing light-sensitive color photographic materials, there has been a strong desire to develop a useful color fog inhibitor which has a high scavenging ability and a strong resistance against diffusion in order to produce a color photographic material of higher quality.

Accordingly, an object of this invention is to provide a useful color fog inhibitor which has excellent scavenging ability, which is capable of effectively preventing color fog or stain from occurring in a small amount, which does not easily move in a hydrophilic layer before, during or after a coating step or during development and which can be readily synthesized. Another object is to provide a light-sensitive color photographic material containing such useful color fog inhibitor.

Other objects of this invention will be apparent from the description given hereinafter.

We have found that the afore-mentioned objects and other objects can effectively be achieved by a light-sensitive color photographic material comprising a support and at least one hydrophilic colloid layer coated thereon which comprises a light-sensitive silver halide emulsion and an image dye forming substance associated with said silver halide emulsion and a hydroquinone compound or a precursor thereof which has at least one electron attractive group in the benzene nucleus and which is non-diffusible under alkaline condition, after development; in particular a non-diffusible hydroquinone compound which has in the benzene nucleus at least one electron attractive group selected from an acyl group, nitro group, cyano group, formyl group, alkyl group having at least one halogen atom at α- or β-position,

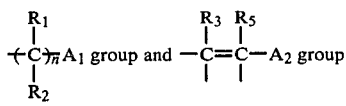

wherein $A_1$ and $A_2$ independently represent an acyl group, nitro group, cyano group or formyl group, $R_1$, $R_2$, $R_3$, and $R_5$ independently represent a hydrogen atom, alkyl group, alkenyl group, aryl group, cycloalkyl group, cycloalkenyl group or halogen atom and n represents 1 or 2, or a precursor thereof which can produce such hydroquinone compound under alkaline condition. The 'hydroquinone precursor' includes, for example, a compound in which one or two hydroxyl groups of a hydroquinone compound are protected with a group such as

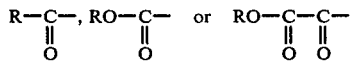

(wherein R represents an aliphatic group), as described in the U.S. Patent Ser. No. 16,029 filed on Feb. 28, 1979.

These precursors form the hydroquinone compounds of the present invention under alkaline condition of normally more than $10^{-5}$ mol/l of hydroxidion concentration, preferably $10^{-4}$ to 2 mol/l of hydroxidion concentration, as produced by, for example, a color developing solution in the color developing process or an alkaline processing composition in the color diffusion transfer process.

As the hydroquinone compounds or the hydroquinone precursors according to the present invention, those in which the electron attractive group is selected from an acyl, nitro, cyano, trihalogenomethyl (for example, trifluoromethyl) and formyl groups are preferably included and, more specifically, a compound of the following general formula (I) is preferable because of its strong scavenging ability: General formula (I)

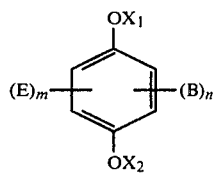

wherein E represents an acyl, nitro, cyano, formyl or trihalogenomethyl group, B represents a monovalent group or atom, $X_1$ and $X_2$ independently represent a hydrogen atom or protective group which can be split off under alkaline condition, m represents an integer from 1 to 4 and n represents an integer from 0 to 3, provided that the sum of carbon atoms in $(E)_m$ and $(B)_n$ is between 12 and 80, the sum of m and n is from 1 to 4 and said E and B may be the same or different when m and n independently are more than 2. This is applicable also to the description given later. Particularly preferable electron attractive group includes an acyl, nitro, cyano and formyl groups.

Preferably acyl group of E includes a group represented by the formula $-COR_7$ or $-SO_2-R_8$ [where $R_7$ represents an alkyl, alkenyl, cycloalkyl, or cycloalkenyl group (each of these groups may have a substituent such as a halogen atom, e.g. chlorine, bromine or fluorine, an aryl group, e.g. p-dodecylcarbonylaminophenyl group, etc.), or aryl group which may have a substituent such as a halogen atom, e.g. chlorine or bromine, alkyl group, alkoxy group, nitro group, etc. and $R_8$ represents an aryl group which may have a substituent such as a halogen atom, e.g. chlorine or bromine, alkyl group, nitro group, alkoxy group, carbamoyl group, e.g. phenylcarbamoyl group, etc.]. Among the above-mentioned groups for $R_7$, an alkyl, cycloalkyl, alkenyl or aryl group and particularly an alkyl group having 1 to 17 carbon atoms and more particularly a lower alkyl group having 1 to 3 carbon atoms (e.g. methyl, ethyl, monochloromethyl or isopropyl) is preferable. Among alkyl groups having 3 to 17 carbon atoms, a branched alkyl group particularly a secondary alkyl group is preferable. The most useful alkyl group is methyl which may be substituted by, for example, halogen atom like monochloromethyl.

As B, a halogen atom such as chlorine or bromine can be mentioned as a preferable monovalent atom and an alkyl, cycloalkyl, alkenyl, aryl, alkoxy, aryloxy, carbamoyl, sulfamoyl and amido groups (each of these groups may have a substituent) as a preferable monovalent group.

The above-mentioned alkyl group includes, for example, an alkyl group, which may be straight or branched, having 1 to 36 carbon atoms such as sec-dotriacontyl, sec-eicosyl, sec-octadecyl, sec-hexadecyl, sec-dodecyl, sec-decyl, sec-octyl, sec-butyl, n-pentadecyl, sec-undecyl, n-propyl, ethyl, methyl, tert-eicosyl, tert-heptadecyl, tert-dodecyl, tert-decyl, tert-octyl, tert-amyl, tert-hexyl or tert-butyl, and a substituted alkyl such as a benzyl group which may further be substituted by a lower alkoxy group or halogen atom (for example, benzyl, α,α-dimethylbenzyl, α-ethyl-p-methoxybenzyl, α-methyl-o-methylbenzyl, α-methylbenzyl, α-methyl-m-chlorobenzyl and α-methyl-p-methylbenzyl). The cycloalkyl group includes, for example, 1-methylcyclohexyl group and the amido group includes, for example, α-ethyl-α-(2,4-di-tert-amylphenoxy)acetamido and α-(2-tetradecyl-4-chlorophenoxy)acetamido groups.

Among the above-mentioned various groups for B, those which are particularly preferable are alkyl groups and among them, those having 8 to 36, particularly 10 to 22 carbon atoms are preferable and further branched ones particularly secondary alkyl groups are preferable.

In the above general formula (I), a preferable protective group represented by $X_1$ or $X_2$ is selected from a group consisting of

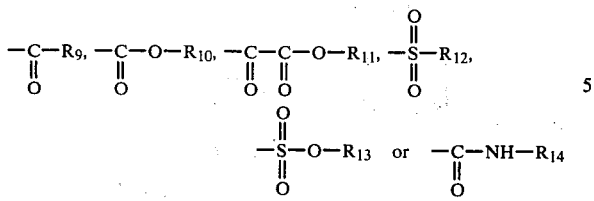

where $R_9$, $R_{10}$, $R_{11}$, $R_{12}$, $R_{13}$ and $R_{14}$ independently represent an alkyl group, cycloalkyl group, alkenyl group or aryl group (each group may be substituted by a halogen atom such as chlorine, bromine or fluorine).

Compounds which are preferably used in the present invention and are represented by general formula (I) are those in which m is 1, n is 0, 1 or 2, E is a nitro, —CO—(alkyl) (said alkyl having 1 to 7 carbon atoms), cyano or formyl group, at least one B is an alkyl group having 8 to 36 carbon atoms provided that the sum of carbon atoms in $(E)_m$ and $(B)_n$ being between 12 and 80, preferably 16 and 80 and particularly said at least one alkyl group as B or —CO—(alkyl) (said alkyl group having from 1 to 17 carbon atoms) is a branched alkyl group, in particular a secondary alkyl group. More preferably, m is 1, n is 1 or 2, E is a nitro, —CO—(lower alkyl having 1 to 3 carbon atoms), cyano or formyl group and at least one B is, in view of excellent dispersibility, a branched alkyl group particularly a secondary alkyl group having 8 to 36 carbon atoms, and the sum of carbon atoms of $(B)_n$ is preferably between 12 and 72 particularly 16 and 72 and more preferably, at least one of $(B)_n$ has from 8 to 36 carbon atoms.

The most preferable compounds in the above general formula (I) are those in which m is 1, n is 1 or 2, E is nitro or acetyl group, $X_1$ and $X_2$ are both hydrogen atoms and at least one B is a secondary alkyl group having 10 to 22 carbon atoms provided that the sum of carbon atoms of $(B)_n$ being between 16 and 44.

While the use of hydroquinone compounds having on the benzene nucleus an electron attractive group as the color fog inhibitor is disclosed in U.S. Pat. Nos. 2,403,721, 2,675,314, 2,701,197 and 3,142,564, British Pat. Nos. 891,158 and 1,156,167, Japanese OPI Patent Publication Nos. 49-134327/1974 and 51-9828/1976, such hydroquinone compounds specifically mentioned in these patents or patent publications are those having a sulfo or carboxyl group attached to a benzene nulceus directly or through an alkylene group. Such hydroquinone compounds have such drawbacks that, because they have a strongly hydrophylic group, they have less resistance against diffusion, their operability is poor since a dispersion solution thereof shows extreme fall in pH, and when coated as a layer, they often cause fine coating defects. On the other hand, such hydroquinone compounds having an alkylcarbonyl group in a benzen ring are known but they are known only as intermediates for the synthesis of n-alkyl hydroquinones as described in U.S. Pat. No. 2,728,659 and no description is given as to their effects.

The hydroquinone compounds and precursors thereof advantageously used in the present invention are exemplified below.

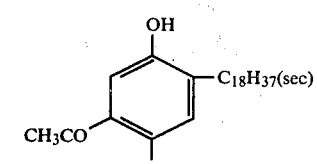 1.

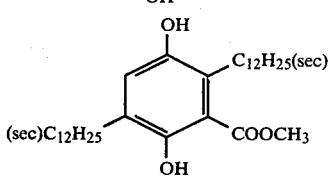 2.

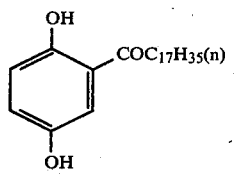 3.

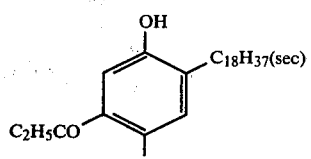 4.

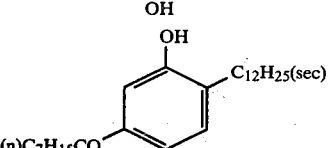 5.

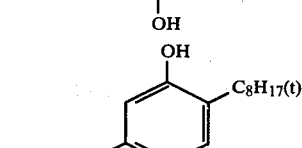 6.

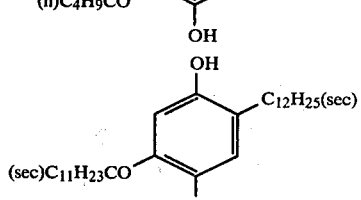 7.

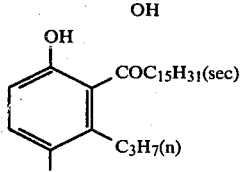 8.

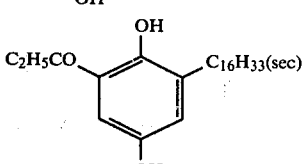 9.

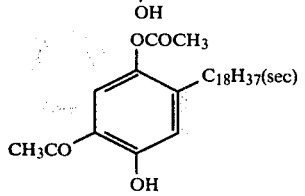 10.

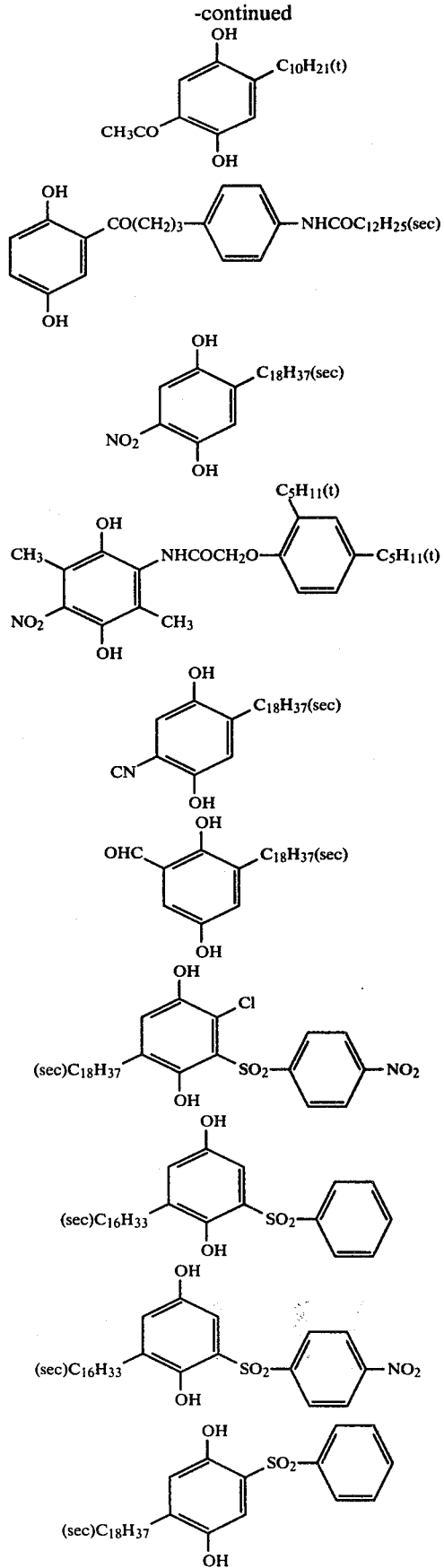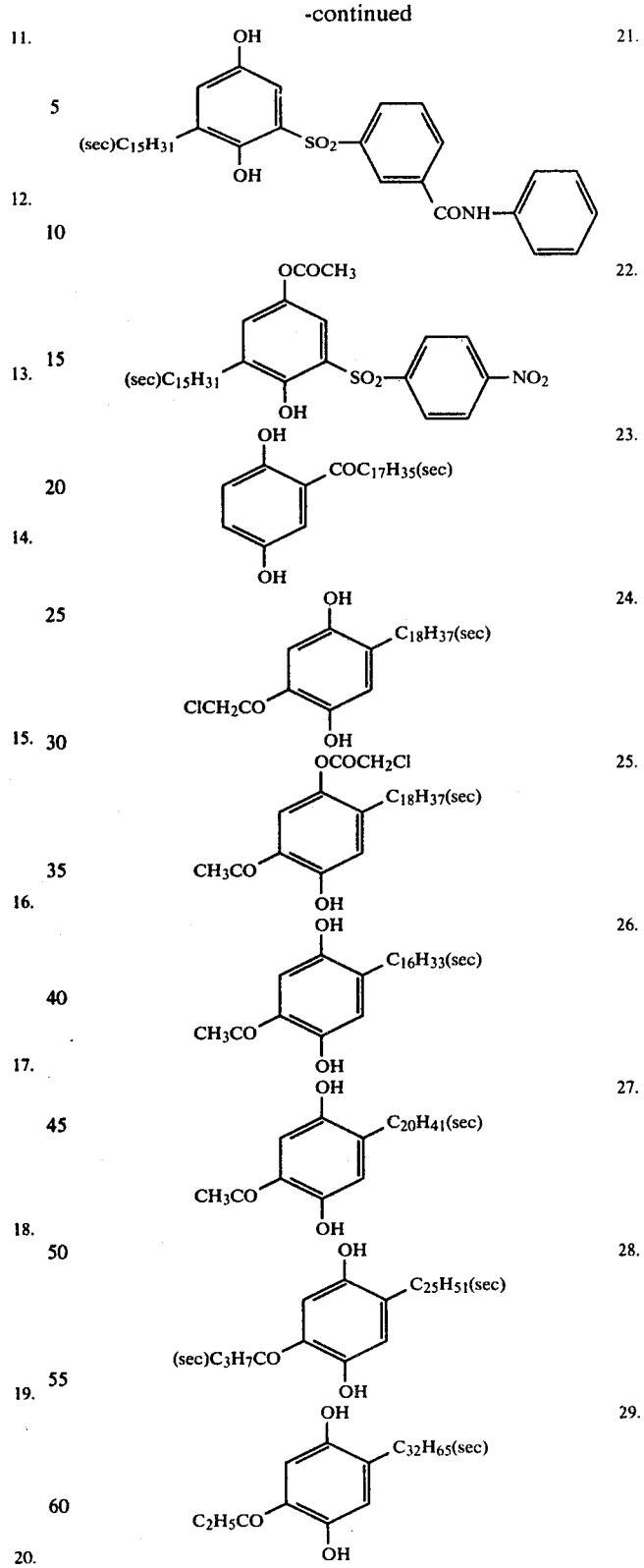
These hydroquinone compounds and the precursors thereof used in this invention can be prepared according to various known and the like processes. For example, they are prepared according to a process which comprises acylation of a hydroxyl group in a hydroquinone derivative followed by Fries rearrangement to obtain a hydroquinone compound containing an acyl group on a benzene nucleus or a process which comprises acylation of a di-lower alkyl ether of alkyl hydroquinone in the presence of a catalyst such as aluminum chloride and then removal of the lower alkyl groups with hydrobromic acid or the like. Further, according to the description of Journal of the American Chemical Society, 66, 798–801 (1944), a di-lower alkyl ether of alkyl hydroquinone is nitrated or cyanated and then the lower alkyl groups are removed to give a hydroquinone compound containing nitro group or cyano group. Alternatively, it is possible according to the description of J. A. C. S., 82, 1928–1935 (1960) to directly prepare a hydroquinone compound containing an acyl group by using a carboxylic acid and boron trifluoride. Furthermore, the preparation is possible according to the process described in Helvetica Chimica Acta, 30, 124 (1947). Some synthesis examples for hydroquinone compounds and the precursors thereof used in this invention will be given below.

Synthesis Example 1

Synthesis of 2-sec-octadecyl-5-acetyl-hydroquinone (1) Synthesis of 2-sec-octadecylhydroquinone dimethyl ether;

33.5 g of p-dimethoxy benzene, 68.0 g of 1-octadecene and 7.7 g of dry silica alumina were heated at 225°–240° C. for 6 hours. After being allowed to cool, the reaction mixture was extracted with ethyl acetate and filtered. The solvent was distilled off under reduced pressure and the residue was distilled under reduced pressure to give 50.0 g of 2-sec-octadecylhydroquinone dimethyl ether having b.p. 220°–223° C./2.5 mmHg.

Alternatively, the above 2-sec-octadecylhydroquinone dimethyl ether was also obtained by the etherification of 2-sec-octadecylhydroquinone. Thus, 5.0 g of 2-sec-octadecylhydroquinone were dissolved in 50 ml of acetone and 1.2 g sodium hydroxide were added. After the dropwise addition of 3.8 g of dimethyl sulfate at room temperature, the reaction mixture was refluxed for 2 hours. The solvent was distilled off under reduced pressure and the residue was extracted with ether. After being washed with water and dried, the residue was distilled under reduced pressure to give 2.0 g of 2-sec-octadecylhydroquinone dimethyl ether having b.p. 200°–206° C./0.6 mmHg. IR and NMR data of both products were completely identical.

(2) Synthesis of 2-hydroxy-4-sec-octadecyl-5-methoxyacetophenone;

To 100 ml of carbon disulfied were added 4.4 g of aluminum chloride and further 2.2 g of acetyl chloride were added with stirring. Under cooling with ice, a solution of 10 g of 2-sec-octadecylhydroquinone in 10 ml of carbon disulfide was added dropwise over 20 minutes. Thereafter, stirring was continued for one hour at room temperature and then the solution was refluxed for 7 hours. After the solvent was distilled off, the residue was decomposed with ice-hydrochloric acid, extracted with ether. The ether solution was washed with water and dried. Then, the solvent was distilled off to give 10.3 g of 2-hydroxy-4-sec-octadecyl-5-methoxyacetophenone as dark green oil. The structure of the above product was confirmed by means of IR and NMR data.

(3) Synthesis of 2-sec-octadecyl-5-acetylhydroquinone;

After refluxing 10.3 g of 2-hydroxy-4-sec-octadecyl-5-methoxyacetophenone, 24.2 ml of 47% hydrobromic acid and 217 ml of acetic acid for 8 hours, the solvent was distilled off under reduced pressure. The residue was extracted with ether and thereafter the ether solution was washed with water and dried. The solvent was distilled off under reduced pressure and then the residue was dissolved in benzene. The benzene solution was then treated with active carbon and the solvent was distilled off under reduced pressure to give 8.0 g of the end product in the form of dark green semi-solid. The structure of the above product was confirmed by means of IR, NMR and elemental analysis data. Elemental analysis:

|  | C% | H% |
| --- | --- | --- |
| Calculated | 77.17 | 10.96 |
| Found | 77.36 | 11.10 |

Alternatively, demethylation of 2-hydroxy-4-sec-octadecyl-5-methoxyacetophenone could also be carried out with boron tribromide. That is, 1.0 g 2-hydroxy-4-sec-octadecyl-5-methoxyacetophenone was dissolved in 10 ml of benzene and 0.5 ml of boron tribromide was added dropwise under cooling with water. After stirring for one hour at room temperature, methyl alcohol was added to decompose excess boron tribromide. The resulting solution was extracted with ether. The ether solution was then washed with water and dried. Thereafter, the solvent was distilled off under reduced pressure to give 0.82 g of the yellowish green end product. IR and NMR data of both products were completely identical.

Synthesis Example 2

Synthesis of 2,5-di-sec-dodecyl-3-acetylhydroquinone (1) Synthesis of 1,4-di-acetoxy-2,5-di-sec-dodecylbenzene;

To 8.9 g of 2,5-di-sec-dodecylhydroquinone and 4.1 g of acetic anhydride was added one drop of concentrated sulfuric acid and the mixture was stirred at 90° C. for 15 minutes. The reaction mixture was admixed into ice and extracted with benzene. The benzene solution was washed with water and dried. The solvent was distilled off under reduced pressure to give 7.5 g of the end product as pale yellow oil. The structure of the product was determined by means of IR, NMR data.

(2) Synthesis of 2,5-di-sec-dodecyl-3-acetylhydroquinone;

To 4.5 g of 1,4-di-acetoxy-2,5-di-sec-dodecylbenzene were added 3.0 g of aluminum chloride and the mixture was heated for 20 minutes at 135°–145° C. To the reaction mixture ice-hydrochloric acid was added and extraction with ethyl acetate was effected. After washing with water and drying, the solvent was distilled off under reduced pressure and the residue was purified through silica gel column chromatography to give 2.0 g of the end product as dark green oil. The structure of the product was determined by means of IR, NMR and elemental analysis data.
Elemental analysis:

|  | C% | H% |
| --- | --- | --- |
| Calculated | 78.63 | 11.55 |

-continued

|  | C% | H% |
|---|---|---|
| Found | 78.48 | 11.41 |

Synthesis Example 3

Synthesis of 2-sec-octadecyl-5-nitrohydroquinone (1) Synthesis of 2-sec-octadecyl-5-nitrohydroquinone dimethyl ether 10.0 g of 2-sec-octadecylhydroquinone were dissolved in 50 ml of glacial acetic acid and at 20° C., a mixture of 4.1 ml of concentrated nitric acid (d=1.42) and 4.1 ml of water was added dropwise. After stirring for 3 hours, the above solution was added to water and extracted with ethyl acetate. After washing with water and drying, the solvent was distilled off under reduced pressure and the residue was purified through silica gel column chromatography. As the developing solvent, benzene/n-hexane (1:1) was used. 9.3 g Of the end product were obtained as yellowish brown oil. The structure was determined by means of IR and NMR data.

(2) Synthesis of 2-sec-octadecyl-5-nitrohydroquinone

To 5.0 g of 2-sec-octadecyl-5-nitrohydroquinone dimethyl ether and 135 ml of glacial acetic acid were added 15 ml of 47% hydrobromic acid and the mixture was heated with reflux for 10 hours. After being allowed to cool, the mixture was added to water and then extracted with ether. After washing with water and drying, the solvent was distilled off under reduced pressure and the residue was purified through silica gel column chromatography. As the developing solvent ,benzene/n-hexane (1:1) was used. The end product was obtained in 1.7 g as yellowish brown semisolid. The structure was determined by means of IR, NMR and elemental analysis data. Elemental analysis:

|  | C% | H% | N% |
|---|---|---|---|
| Calculated | 70.72 | 10.14 | 3.44 |
| Found | 70.91 | 10.23 | 3.29 |

Synthesis Example 4

Synthesis of 2-n-octadecyl-4-propionyloxyphenol

To 5.2 g of n-octadecanoylhydroquinone and 6.0 g of anhydrous propionic acid were added 1.5 ml of concentrated sulfuric acid and thereafter the mixture was heated on an oil bath at 140° C. for 15 minutes. After being allowed to be cooled, the mixture was added to ice and extracted with ethyl acetate. The extract was washed with water and dried. Purification through silica gel column chromatography [developing solvent: benzene/acetone (9:1)] gave 2.3 g of the end product having m.p. 75°-78° C. Elemental analysis:

|  | C% | H% |
|---|---|---|
| Calculated | 74.95 | 10.25 |
| Found | 75.13 | 10.09 |

The hydroquinone compounds and the precursor thereof used in the present invention thus prepared can effectively reduce formation of color fog or color stain when used in color photographic materials and, in particular, they are suitably used in multi-color photographic materials.

The hydroquinone compounds used in this invention are made inactive while they convert undesirable oxidation product of the afore-mentioned color developing agent as used for ordinary color development or other developing agent such as a DRR compound into the original form thereof or into a form that is not reactive with an image dye forming substance.

The light-sensitive color photographic material according to the invention comprises a support and at least one hydrophilic colloid layer coated thereon which comprises a light-sensitive silver halide emulsion and an image dye forming substance associated with said emulsion. Said emulsion and the image dye forming substance may be present either in the same hydrophilic colloid layer or in two or more separate hydrophilic colloid layers. As such hydrophilic layers, in addition to the above-mentioned emulsion layer and the image dye forming substance containing layer, there can be mentioned, depending upon the uses of said light-sensitive color photographic material and the properties of the emulsion layer, for example, a layer positioned between the light-sensitive silver halide emulsion layer and the layer containing an image dye forming substance associated with said emulsion layer, an inter-layer, a protective layer, an anti-halation layer, a layer containing physical development nucleus, an image-receiving layer, an opacifying layer, a light-reflecting layer, a sub layer, a neutralizing layer, a timing layer and the like.

The hydroquinone compounds and the precursor thereof according to the present invention can be added to various hydrophilic layers of the above-mentioned light-sensitive color photographic materials, for example, light-sensitive silver halide emulsion layer, image dye forming substance containing layer, inter-layer, protective layer, anti-halation layer, opacifying layer, layer containing physical development nucleus etc., and preferable to the light-sensitive silver halide emulsion layer, image dye forming substance containing layer, inter-layer or protective layer. Particularly preferably, they are added to non-light-sensitive layers, for example, protective layer, image dye forming substance containing layer or inter-layer. Further, the hydroquinone compounds and the precursor thereof may be added to two or more of the above-mentioned layers and they may be used singly or in combination.

The hydroquinone compounds or precursors thereof used in this invention may be used at various concentrations depending upon the nature or type of the light-sensitive silver halide photographic material or emulsion, or image dye forming substances used, layer to which they are added or factors deriving from development treatments, but generally used at a concentration of $1 \times 10^{-3}$ to $5 \times 10^{-1}$ mol per mol of silver halide. Particularly, when the hydroquinone compound or precursor thereof is added to the silver halide emulsion layer or image dye forming substance containing layer, a concentration of $1 \times 10^{-3}$ to $1 \times 10^{-1}$ mol per mol of silver halide is preferable and further, when the hydroquinone compound or precursor thereof is particularly added to the image dye forming substance containing layer, a concentration ranging from $1 \times 10^{-2}$ to $2 \times 10^{-1}$ mol per mol of the image dye forming substance is preferable. Further, when added to the inter-layer or protective layer, $5 \times 10^{-3}$ to $2 \times 10^{-1}$ mol per mol of silver halide employed in the light-sensitive photographic material is preferable. Furthermore, when added to the inter-layer or protective layer of a light-sensitive photographic material for use in the color diffusion transfer process where a highly alkaline processing composition is applied, a concentration of $2\times10^{-2}$ to $2\times10^{-1}$ mol per mol of the silver halide as used is more preferable.

In the present invention the hydroquinone compound or the precursor thereof is incorporated in a hydrophilic layer of light-sensitive color photographic material in an optional combination, for example, two or more of the hydroquinone compounds such as 2-acetyl-5-sec-octadecylhydroquinone and 2-acetyl-5-sec-hexadecylhydroquinone, two or more of the hydroquinone precursors, one or more of each of the hydroquinone compounds and their precursors, or one or more of the hydroquinone compounds or the precursor thereof used in the present invention and one or more of hydroquinone compounds or the precursor thereof which are outside the present invention, may be used, and thereby better dispersion stability and the effect as is suggested in the Research Disclosure 152, page 19 can be obtained.

Furthermore, by the use of the precursors of hydroquinone compounds singly or in combination with the hydroquinone compounds, there was attained an effect which was unknown heretofore is stated in detail in the afore-mentioned the U.S. Pat. Ser. No. 16,029 and in this sense, use of the hydroquinone compounds according to the present invention and/or hydroquinone precursors according to the present invention is also useful. When used in combination, each of the hydroquinone compounds and their precursors may be added either to the same layer or to a separate layer.

The hydroquinone compounds and/or their precursors according to the present invention can be added to a light-sensitive color photographic material by being dispersed in the hydrophilic colloid layer. As such method for dispersion, any known method is used and, for example, the following methods are useful:

1 A method wherein a hydroquinone compound and/or its precursor according to this invention is dissolved in a substantially water-insoluble high boiling solvent and finely dispersed in the hydrophilic protective colloid.

Particularly useful high boiling solvents include N-n-butylacetanilide, diethyl lauramide, dibutyl lauramide, dibutyl phthalate, tricresyl phosphate, N-dodecyl pyrrolidone, etc.

Further, in order to assist the above dissolution, a low boiling solvent or an organic solvent that is readily soluble in water can be used.

As such low boiling solvent, ethyl acetate, methyl acetate, cyclohexanone, acetone, methanol, ethanol, tetrahydrofuran, etc. can be used and as such organic solvent that is readily soluble in water, 2-methoxy ethanol, dimethyl formamide, etc. can be used. These low boiling solvent and organic solvent readily soluble in water can be removed by washing with water or by drying after coating.

2 A process wherein to a solution of the hydroquinone compound and/or its precursor according to the present invention in a water-miscible organic solvent are added slowly to a chargeable polymer latex and water sufficient to make said hydroquinone compound and/or its precursor in the above solution insoluble to charge thereby the above hydroquinone compound and/or its precursor in the chargeable polymer latex particles.

With regard to said water-miscible organic solvent and chargeable polymer latex, Japanese OPI Patent Publications No. 51-59942/1976 and 51-59943/1976 provide a detailed explanation.

3 A process wherein the hydroquinone compound and/or its precursor according to the present invention is mechanically ground into fine particles by using a sand grinder or colloid mill and then dispersed in the hydrophilic colloid.

In the present invention, while a variety of dispersion method can optionally be used, the process 1 is preferable. Further, when two or more compounds are used, each compound may be dispersed independently or mixed together before, during or after the dispersion.

The "image dye forming substance" used in the light-sensitive color photographic material of this invention is usually one which is ordinarily known, e.g., a compound that forms an image dye by the reaction with the oxidation product of a silver halide developing agent or a compound which is able to release a diffusible dye or its precursor under alkaline condition by the reaction (for example, redox reaction) with said oxidation product.

As such image dye forming substance, a variety of compounds are known in the art and among them, those which are conveniently used are 1 a substantially colorless compound which is able to form an image dye by the coupling reaction with the oxidation product of the above-mentioned silver halide developing agent, 2 a compound wich is able to release a diffusible dye or its precursor as a result of the coupling reaction with the above oxidation product and 3 a compound which is able to release a diffusible dye or its precursor under alkaline condition as a result of the oxidation-reduction reaction (usually known as redox reaction) with the above oxidation product. These image dye forming substances are desirably non-diffusible ones which contain in the molecule a hydrophobic group usually called at a ballast group.

In general, the image dye forming substances classified as group 1 are known as color-forming couplers. Although such couplers may be either 4-equivalent type or 2-equivalent type based on the silver ion, the 2-equivalent type coupler is preferable. Further, there may be used a colored coupler having color correction effect or so-called DIR coupler (Development Inhibitor Releasing coupler) which can release a development inhibitor on the reaction with the oxidation product of a developing agent.

As a yellow coupler, those having an open chain ketomethylene group can be used and especially benzoylacetanilide type couplers and pivaloylacetanilide type couplers are conveniently used. Specific examples of yellow couplers are described in U.S. Pat. Nos. 2,875,057, 3,265,506, 3,277,155, 3,408,194, 3,415,652, 3,447,928 and 3,664,841; Japanese Patent Publication No. 49-13576; Japanese Pat. OPI Publication Nos. 48-29432/1973, 48-66834/1973, 49-10736/1974, 49-122335/1974, 50-28834/1975 and 50-132926/1975.

Specific examples of particularly useful yellow couplers are as follows:

α-(4-carboxyphenoxy)-α-pivalyl-2-chloro-5-[γ-(2,4-di-tert-amylphenoxy)butylamino]acetanilide, α-pivalyl-2-chloro-5-[γ(2,4-di-tert-amylphenxoy)butylamino]acetanilide, α-benzoyl-2-chloro-5-[α-(dodecyloxycarbonyl)ethoxycarboxyl]acetanilide, α-(4-carboxyphenoxy)-α-pivalyl-2-chloro-5-[α-(3-pentadecylphenoxy)butylamino]acetanilide, α-(1-benzyl-2,4-dioxo-3-imidazolidinyl)-α-pivalyl-2-chloro-5-[γ-(2,4-di-tert-amylphenoxy)-butylamino]acetanilide, α-[4-(1-benzyl-2-phenyl-3,5-dioxo-1,2,4-triazolidinyl)]-α-pivalyl-2-chloro-5-[γ-(2,4-di-tert-amylphenoxy)butylamino]-acetanilide, α-acetoxy-α-{3-[α-(2,4-di-tert-amylphenoxy)-butylamino]benzoyl}-2-methoxyacetanilide, α-{3-[α-(2,4-di-tert-amylphenoxy)butylamino]benzoyl}-2-methoxyacetanilide, α-[4-(4-benzyloxyphenylsulfonyl)phenoxy]-α-pivalyl-2-chloro-5-[γ-(2,4-di-tert-amylphenoxy)-butylamino]acetanilide, α-pivalyl-α-(4,5-dichloro-3-pyridazon-2-yl)-2-chloro-5-[(hexadecyloxycarbonyl)methoxycarbonyl]acetanilide, α-pivalyl-α-[(4-(4-chlorophenyl)-5-oxo-Δ²-tetrazolin-1-yl]-2-chloro-5-[α-dodecyloxycarbonyl)ethoxycarbonyl]-acetanilide, α-(2,4-dioxo-5,5-dimethyloxazolidin-3yl)-α-pivalyl-2-chloro-5-[α-(2,4-di-tert-amylphenoxy)-butyrylamino]acetanilide, α-pivalyl-α-[4-(1-methyl-2-phenyl-3,5-dioxo-1,2,4-triazolidinyl)]-2-chloro-5-[γ-(2,4-di-tert-amylphenoxy)-butyrylamino]acetanilide and α-pivalyl-α- [4-(4-ethyphenyl)-5-oxo-Δ²-tetrazolin-1-yl]-2-chloro-5-[γ-(2,4-di-tert-amylphenoxy)-butyrylamino]-acetanilide.

As magenta couplers, pyrazolone series pyrazolotriazole series, pyrazolinobenzimidazole and indazolone type compounds are used. As the magenta couplers of pyrazolone type, these are used, for example, compounds described in U.S. Pat. Nos. 2,600,788, 3,062,653, 3,127,269, 3,311,476, 3,419,391, 3,519,429, 3,558,318, 3,684,514 and 3,888,680; Japanese OPI Patent Publications No. 49-29639/1974, 49-111631/1974, 49-129538/1974, 50-13041/1974, 51-105820/1975, 52-58533/1977 and 52-80027/1977. As the magenta couplers of pyrazolotriazole series, there are used compounds described in British Pat. No. 1,247,493 and Belgian Pat. No. 792,525. As the magenta couplers of pyrazolinobenzimidazole type, there are used compounds described in U.S. Pat. No. 3,061,432, West German Patent 2,156,111 and Japanese OPI Patent Publication No. 46-60479/1971. Further, as the magenta couplers of indazolone type, compounds described in Belgian Pat. No. 769,116 are used. Specific examples of magenta couplers which are particularly useful in this invention are given below.

1-(2,4,6-trichlorophenyl)-3-[3-(2,4-di-tert-amylphenoxyacetamido)benzoylamino]-5-pyrazolone, 1-(2,4,6-trichlorophenyl)-3-(3-dodecylsuccinimidobenzoylamino)-5-pyrazolone, 4,4'-methylene bis{1-(2,4,6-trichlorophenyl)-3-[3-(2,4-di-tert-amylphenoxyacetamido)benzoylamino]-5-pyrazolone}, 1-(2,4,6-trichlorophenyl)-3-[2-chloro-(3-octadecylsuccinimido)anilino]-5-pyrazolone, 1-(2-chloro-4,6-dimethylphenyl)-3-{3-[α-(3-pentadecylphenoxy)butyrylamino]benzoylamino}-5-pyrazolone, 1-(2,4,6-trichlorophenyl)-3-(2-chloro-5-octadecylcarbamoylanilino)-5-pyrazolone, 3-ethoxy-1-{4-[α-(3-pentadecylphenoxy)-butyrylamino]phenyl}-5-pyrazolone, 1-(2,4,6-trichlorophenyl)-3-(2-chloro-5-tetradecanoylaminoanilino)-5-pyrazolone, 1-(2,4,6-trichlorophenyl)-3-{2-chloro-5-[α-(3-tert-butyl-4-hydroxyphenoxy)tetradecanoylamino]anilino}-5-pyrazolone, 1-(2,4,6-trichlorophenyl)-3-[3-(2,4-di-tert-amylphenoxyacetamido)benzoylamino]-4-acetoxy-5-pyrazolone, 1-(2,4,6-trichlorophenyl)-3-[3-(2,4-di-tert-amylphenoxyacetamido)benzoylamino]-4-ethoxycarbonyloxy-5-pyrazolone, 1-(2,4,6-trichlorophenyl)-3-[3-(2,4-di-tert-amylphenoxyacetamido)benzoylamino]-4-(4-chlorocinnamoyloxy)-5-pyrazolone, 4,4-benzylidene bis[1-(2,4,6-trichlorophenyl)-3{2-chloro-5-[α-(2,4-di-tert-amylphenoxy)-butyrylamino]anilino}-5-pyrazolone], 4,4'-benzylidene bis[1-(2,3,4,5,6-pentachlorophenyl)-3-{2-chloro-5-[γ-(2,4-di-tert-amylphenoxy)-butyrylamino]anilino}-5-pyrazolone], 4,4'-2-chloro-benzylidene bis{1-(2,4,6-trichlorophenyl)-3-[2-chloro-(5-dodecylsuccinimido)anilino]-5-pyrazolone} and 4,4'-methylene bis[1-(2,4,6-trichlorophenyl)-3-{3-[α-(2,4-di-tert-amylphenoxy)butyrylamino]benzoylamino}-5-pyrazolone].

Further, as cyan couplers, derivatives of phenol or naphthol are generally included. These cyan couplers are described in U.S. Pat. No. 2,423,730, 2,474,293, 2,801,171, 2,895,826, 3,476,563, 3,737,316, 3,758,308 and 3,839,044; Japanese OPI Patent Publications No. 47-37425/1972, 50-10135/1975, 50-25228/1975, 50-112038/1975, 50-117422/1975 and 50-130441/1975.

Specific examples of cyan couplers which are particularly useful in this invention are given below.

1-hydroxy-N-[δ-(2,4-di-tert-amylphenoxy)butyl]-2-naphthamide, 2,4-dichloro-3-methyl-6-(2,4-di-tert-amylphenoxyacetamido)phenol, 2,4-dichloro-3-methyl-6-[α-(2,4-di-tert-amylphenoxy)-butyrylamino]phenol, 1-hydroxy-4-(3-nitrophenylsulfonamido)-N-[δ-(2,4-di-tert-amylphenoxy)butyl]-2-naphthamide, 1-hydroxy-4-[(β-methoxyethyl)carbamoyl]methoxy-N-[δ-(2,4-di-tert-amylphenoxy)butyl]-2-naphthamide, 1-hydroxy-4-(isopropylcarbamoyl)methoxy-N-dodecyl-2-naphthamide, 2-perfluorobutyrylamino-5-[α-(2,4-di-tert-amylphenoxy)hexanoylamino]phenol, 1-hydroxy-4-(4-nitrophenylcarbamoyl)oxy-N-[δ-(2,4-di-tert-amylphenoxy)butyl]-2-naphthamide, 2-(α,α,β,β-tetrafluoropropionamido)-5-[α-(2,4-di-tert-amylphenoxy)butyrylamino]phenol, 1-hydroxy-N-dodecyl-2-naphthamide, 1-hydroxy-4-(4-nitrophenoxy)-N-[δ-(2,4-di-tert-amylphenoxy)butyl]-2-naphthamide, 1-hydroxy-4-(1-phenyl-5-tetrazolyloxy)-N-[δ-(2,4-di-tert-amylphenoxy)butyl]-2-naphthamide, 2-(α,α,β,β-tetrafluoropropionamido)-4-β-chloroethoxy-5-[α-(2,4-di-tert-amylphenoxy)butyrylamino]phenol and 2-chloro-3-methyl-4-ethylcarbamoylmethoxy-6-[α-(2,4-di-tert-amylphenoxy)butyrylamino]phenol.

Colored couplers include, for example, compounds described in U.S. Pat. Nos. 2,521,908, 2,801,171, 2,983,608, 3,005,712, 3,034,892, 3,419,391, 3,476,563 and 3,684,514; British Patents Nos. 937,621 and 1,255,111; and Japanese OPI Patent Publications Nos. 48-22028/1973, 49-123625/1974 49-131448/1974, 50-10135/1975 and 50-123341/1975.

DIR couplers include, for example, compounds described in U.S. Pat. Nos. 3,148,062, 3,227,554, 3,701,783 and 3,733,201; British Pat. No. 953,454 and DOS No. 1,800,420.

Particularly useful DIR couplers among the above are specified below.

1-{4-[γ-(2,4-di-tert-amylphenoxy)butyrylamino]-phenyl}-3-piperidinyl-4-(1-phenyl-5-tetrazolylthio)-5-pyrazolone, 1-{4-[α-(3-pentadecylphenoxy)butyrylamino]-phenyl}-3-ethoxy-4-(1-phenyl-5-tetrazolylthio)-5-pyrazolone, 1-hydroxy-4-(1-phenyl-5-tetrazolylthio)-N-(2-tetradecyloxyphenyl)-2-naphthanilide, α-pivalyl-α-(1-phenyl-5-tetrazolylthio)-2-chloro-5-[γ-(2,4-di-tert-amylphenoxy)butyrylamino]acetanilide, 1-hydroxy-4-(1-phenyl-5-tetrazolylthio)-N:[δ-(2,4-di-tert-amylphenoxy)butyl]-2-naphthamide, 1-{4-[α-(2,4-di-tert-amylphenoxy)butyrylamino]-phenyl}-3-pyrrolidino-4-(1-phenyl-5-tetrazolylthio)-5-pyrazolone, 4-(2-benzotriazolyl)-1-(2,4,6-trichlorophenyl)-3-[3-(2,4-di-tert-amylphenoxyacetamide)benzoylamino]-5-pyrazolone, 1-hydroxy-4-(2-benzthiazolylthio)-N-[δ-(2,4-di-tert-amylphenoxy)butyl]-2-naphthamide, α-{3-[γ-(2,4-di-tert-amylphenoxy)butyrylamino]-benzoyl}-α-(1-phenyl-5-tetrazolylthio)-2-chloro-acetanilide, 1-(2,4,6-trichlorophenyl)-3-[3-(2,4-di-tert-amylphenoxyacetamido)benzoylamino]-4-(1-phenyl-5-tetrazolylthio)-5-pyrazolone and 1-hydroxy-4-(2-benztriazolyl)-N-[δ-(2,4-di-tert-amylphenoxy)butyl]-2-naphthamide.

The image dye forming substances classified as group 2 are those known as so-called DDR couplers, and, in general, are such compounds that release as a result of the coupling reaction with the oxidation product of an aromatic primary amine color developing agent a diffusible dye or its precursor under alkaline condition.

As the above DDR couplers, there are included the first type DDR couplers that contain at the so-called active point of a non-diffusible coupler a diffusible dye or its precursor moiety as a substituent which can be split off on the coupling reaction, the second type DDR couplers that contain at the so-called active point of a diffusible coupler a ballast group as the substituent which can be split off on the coupling reaction and the third type couplers which are non-diffusible couplers of phenol type, α-naphthol type, aniline type or α-naphthylamino type and carry a diffusible dye or its precursor at the position adjacent to the active point of such couplers through an amido bonding, (e.g., —NHSO₂— bonding, with the proviso that the nitrogen atom is attached to the position adjacent to the above active point).

As the coupler portion of the above first type and second type DDR couplers, the color forming coupler of each of the afore-mentioned benzoylacetanilide type, pivaloylacetanilide type, pyrazolone type, pyrazolotriazole type, pyrazolinobenzimidazole type, indazolone type, phenol type and naphthol type known heretofore as the color forming couplers can be used. Also indanone type compound, known as a portion of development inhibitor releasing compound can be used as a coupler portion of the above first type DDR couplers. Further, as the diffusible dye portion of the above first type and the third type DDR couplers, those well-known to those skilled in the art can be included and, for example, the dye portion of azo dye, azomethine dye, indoaniline dye, indophenol dye, anthraquinone dye, azopyrazolone dye, alizarin dye, merocyanine dye, cyanine dye, indigoid dye and phthalocyanine dye can be included. Furthermore, as the precursor portion of the diffusible dye, there are included leuco dye (for example, the leuco dye in the dye-developer described in Japanese OPI Patent Publication No. 48-66440/1973), shift type dye (i.e., a dye the absorption spectrum of which shifts hypsochromically or bathochromically after the alkali treatment, e.g., acyloxynaphthylazo dye as described in Japanese patent application No. 51-77148, or a dye the absorption spectrum of which shifts hypsochromically or bathochromically upon dyeing on the image receiving layer) or the like.

If the above second type DDR coupler is used, the dye formed by the coupling reaction serves as the diffusible dye.

Specific examples of the above first type DDR couplers are described, for example, in Japanese OPI Patent Publication No. 49-12302; U.S. Pat. No. 3,227,550, 3,880,658 and 3,765,886; and British Pat. Nos. 904,364 and 904,365.

The first type DDR couplers which are particularly useful in the present invention are exemplified below.

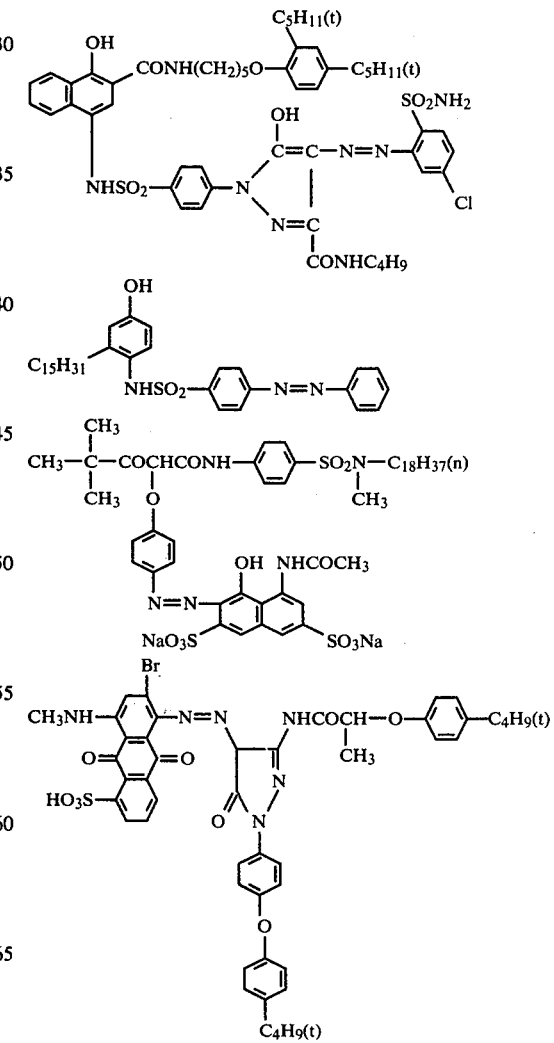

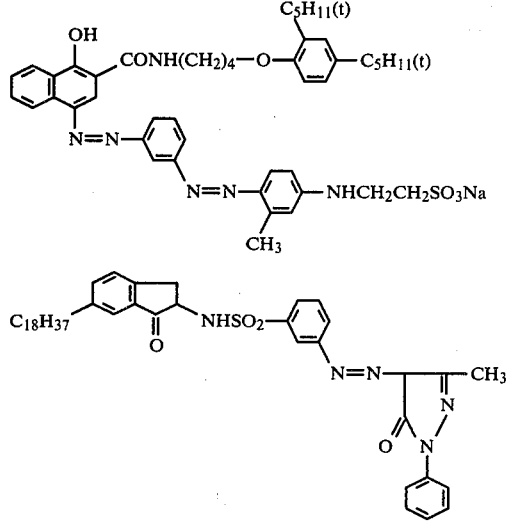

Specific examples of the above second type DDR couplers are described, for example, in U.S. Pat. No. 3,227,550; British Pat. Nos. 904,364, 904,365 and 1,038,331 and Japanese Patent Publication No. 45-15471/1970.

The second type DDR couplers which are particularly useful in the present invention are exemplified below.

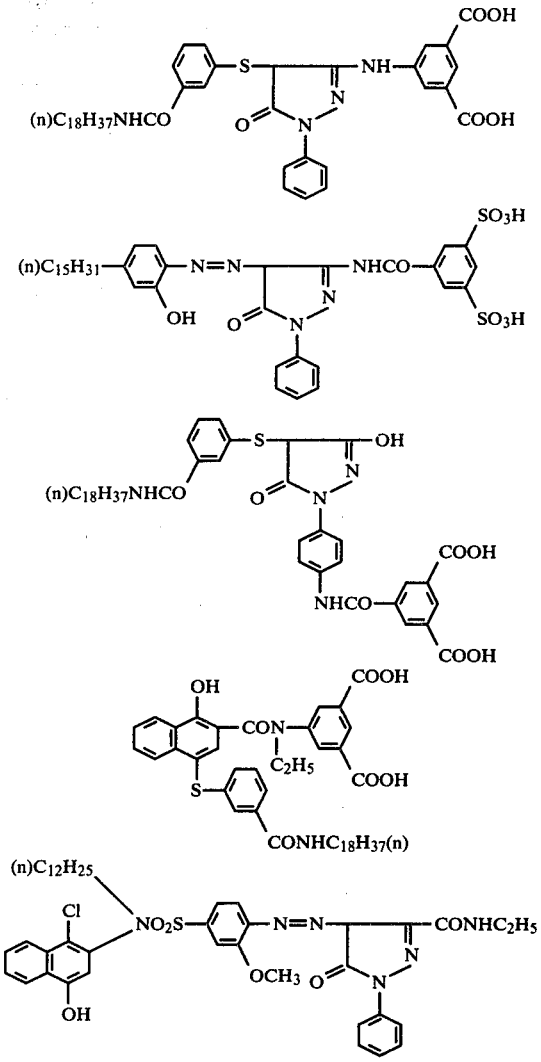

Specific examples of the above third type DDR couplers are described, for example, in U.S. Pat. Nos. 3,443,940 and 3,751,406.

The third type DDR couplers which are particularly useful in the present invention are exemplified below.

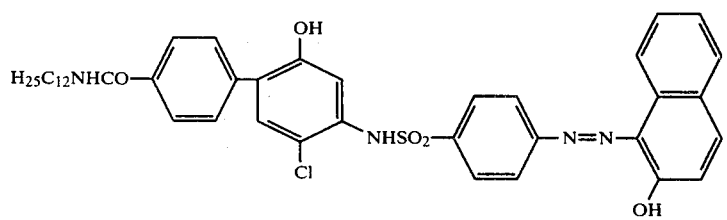

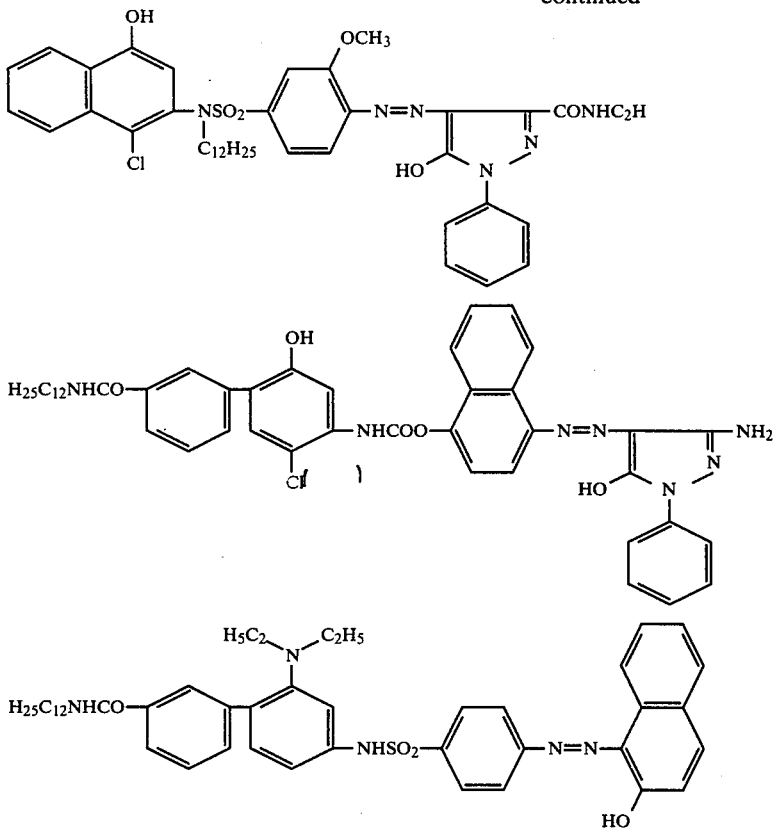

The image dye forming substances classified as group 3 are those known as so-called DRR compounds and representative examples thereof are those wherein the oxidation product of DRR compound formed by the redox reaction is split off under alkaline condition to release a diffusible dye or its precursor or those wherein the oxidation product of DDR compound formed by the redox reaction releases a diffusible dye or its precursor, upon intramolecular ring closure reaction.

Preferable compounds as the former DRR compounds are those represented by the following general formula:

General formula

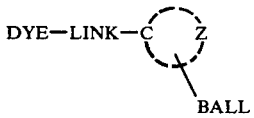

[wherein DYE represents the residue of a diffusible dye or diffusible dye precursor, LINK represents —O—, —S—, —SO₂— or —SO₂NH— (where the nitrogen atom is attached to

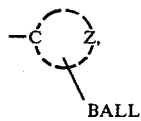

BALL represents a photographically inert ballast group having such size of molecule and/or conformation that enables to make the image dye forming substance non-diffusible under alkaline condition and Z represents a non-metal atom group required for forming together with the carbon atom attached to LINK, a 5- or 6-membered ring which can be split off from the LINK under alkaline condition upon the oxidation-reduction reaction with the oxidation product of the silver halide developing agent].

In the above general formula, a group represented by

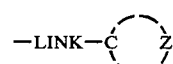

includes —O—(2,5-dihydroxyphenyl) groups, —S—(2,5-dihydroxyphenyl) groups, —SO₂—(2,5-dihydroxyphenyl) groups, —SO₂NH—(p-hydroxyphenyl) groups (where the phenyl group may be fused with a benzene ring, cyclohexane ring), —SO₂NH—(1-hydroxy-2-naphthyl) groups, —SO₂NH—(2-hydroxy-1-naphthyl) groups, —SO₂NH—(2-hydroxy-5-alkoxyphenyl) groups and —SO₂—NH—(3-indolyl) groups.

Specific examples of the former type of DRR compounds are described, for example, in U.S. Pat. Nos. 3,725,062, 3,698,897, 3,728,113, 3,928,312, 3,993,638, 3,932,380, 3,932,381, 3,931,144, 3,929,760 and 3,942,987; French Patent 2,284,140; U.S. Patent Gazette 351,673; Research Disclosure 13024 (1975), ibid 15157 (1976); and Japanese OPI Patent Publications No. 52-8827/1977, 51-104343/1976, 51-113624/1976, 51-109928/1976 and 52-7727/1977.

Further, specific examples of the latter type of DRR compounds are described, for example, in U.S. Pat. Nos. 3,443,943, 3,443,939, 3,443,940 and 3,751,406.

As the diffusible dye or its precursor portion in these DRR compounds, various dyes or precursors thereof previously mentioned herein as the diffusible dyes or precursors thereof for the above-mentioned DDR couplers can be used.
DRR compounds which are particularly useful in the present invention will be exemplified below.
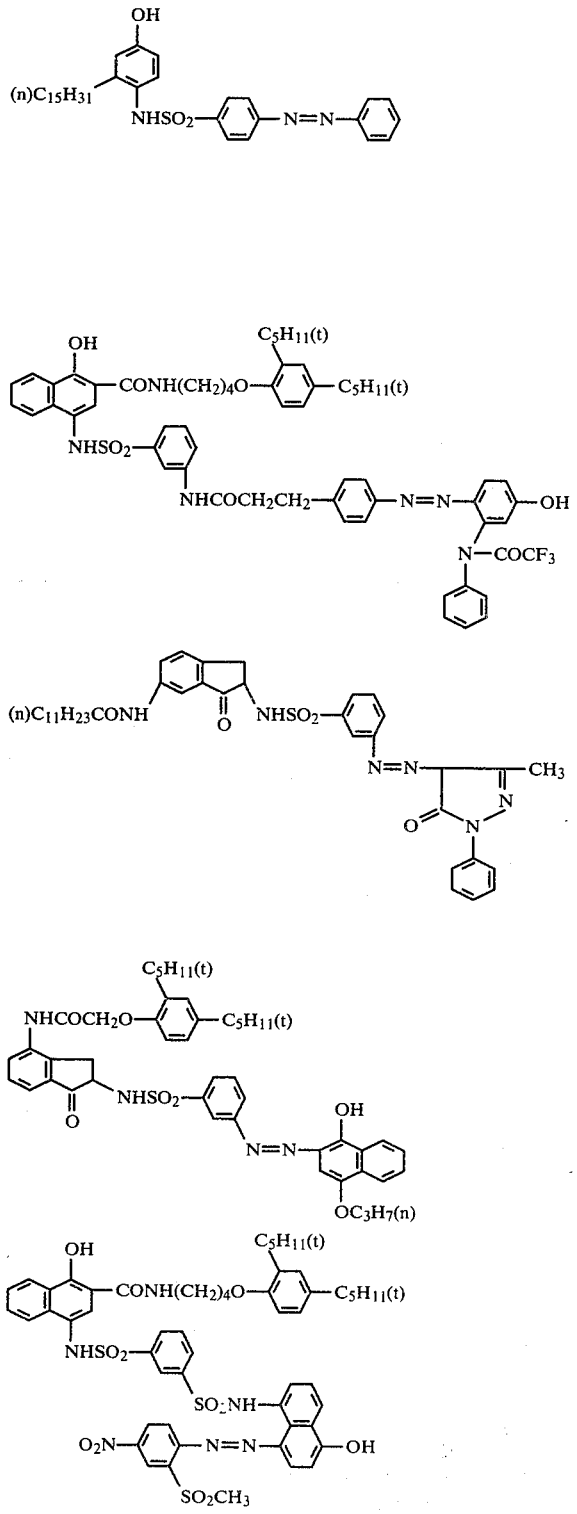
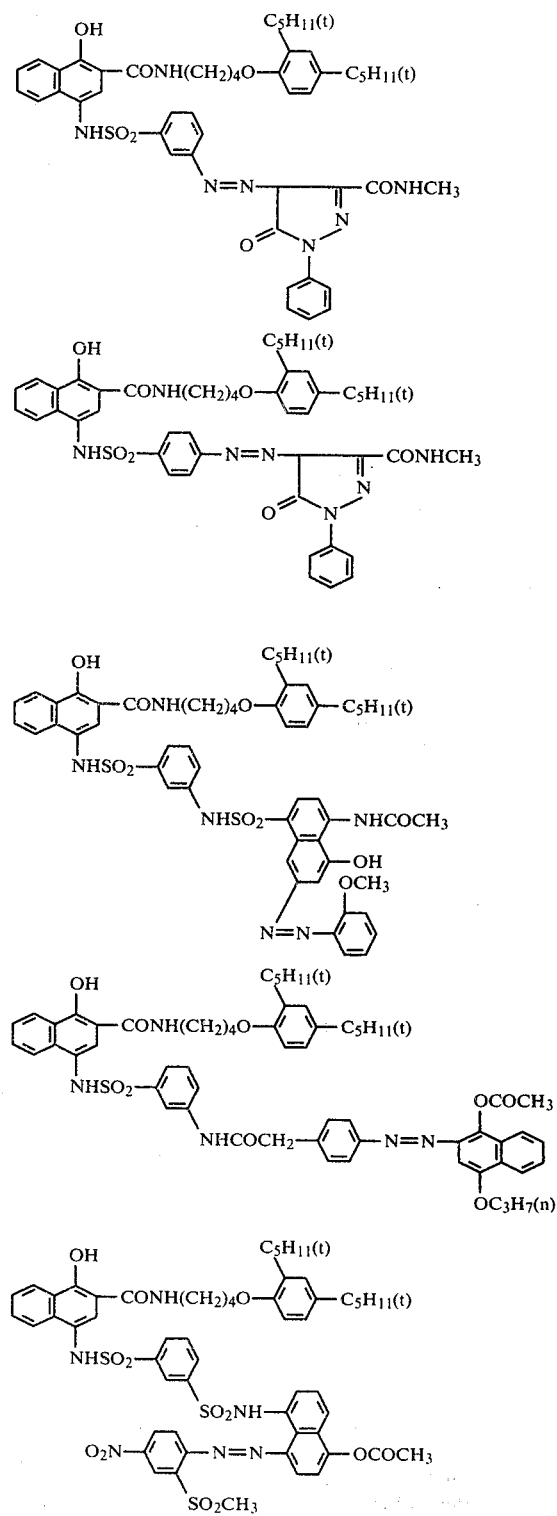

-continued
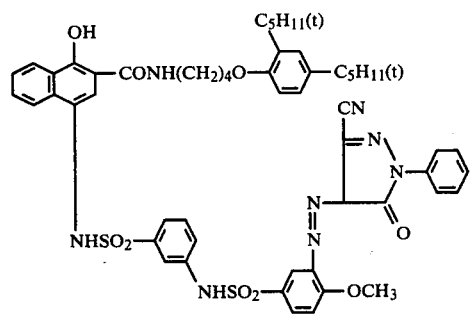
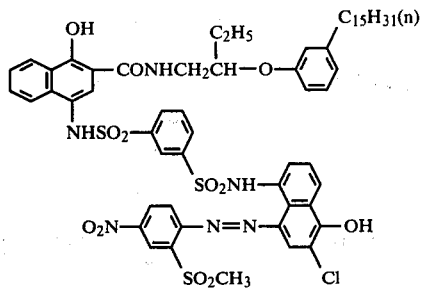
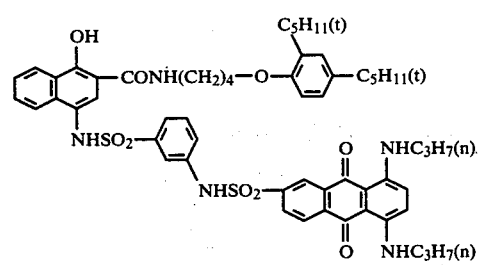
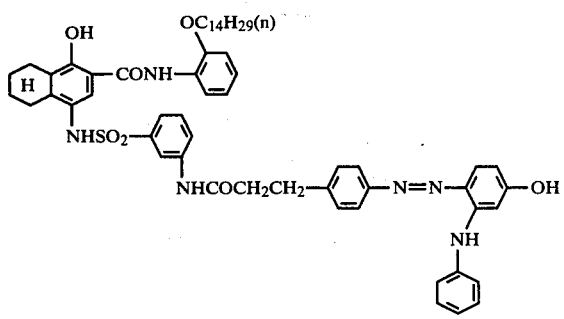
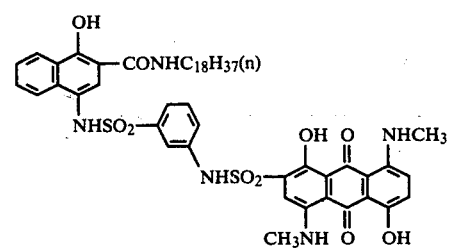
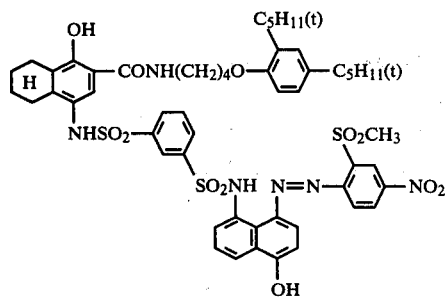
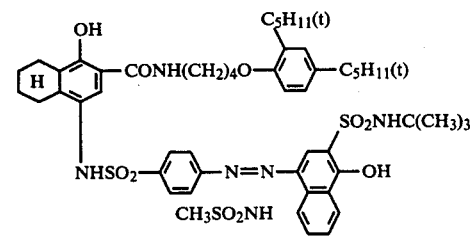
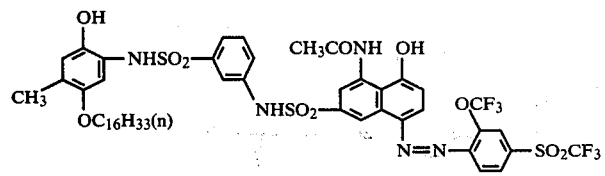
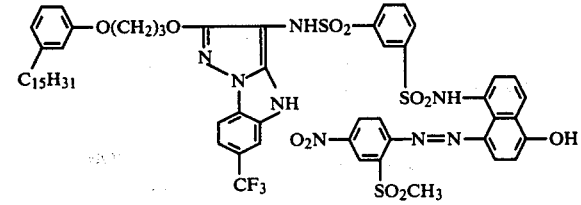
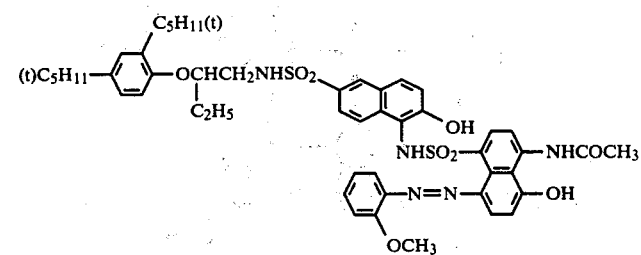

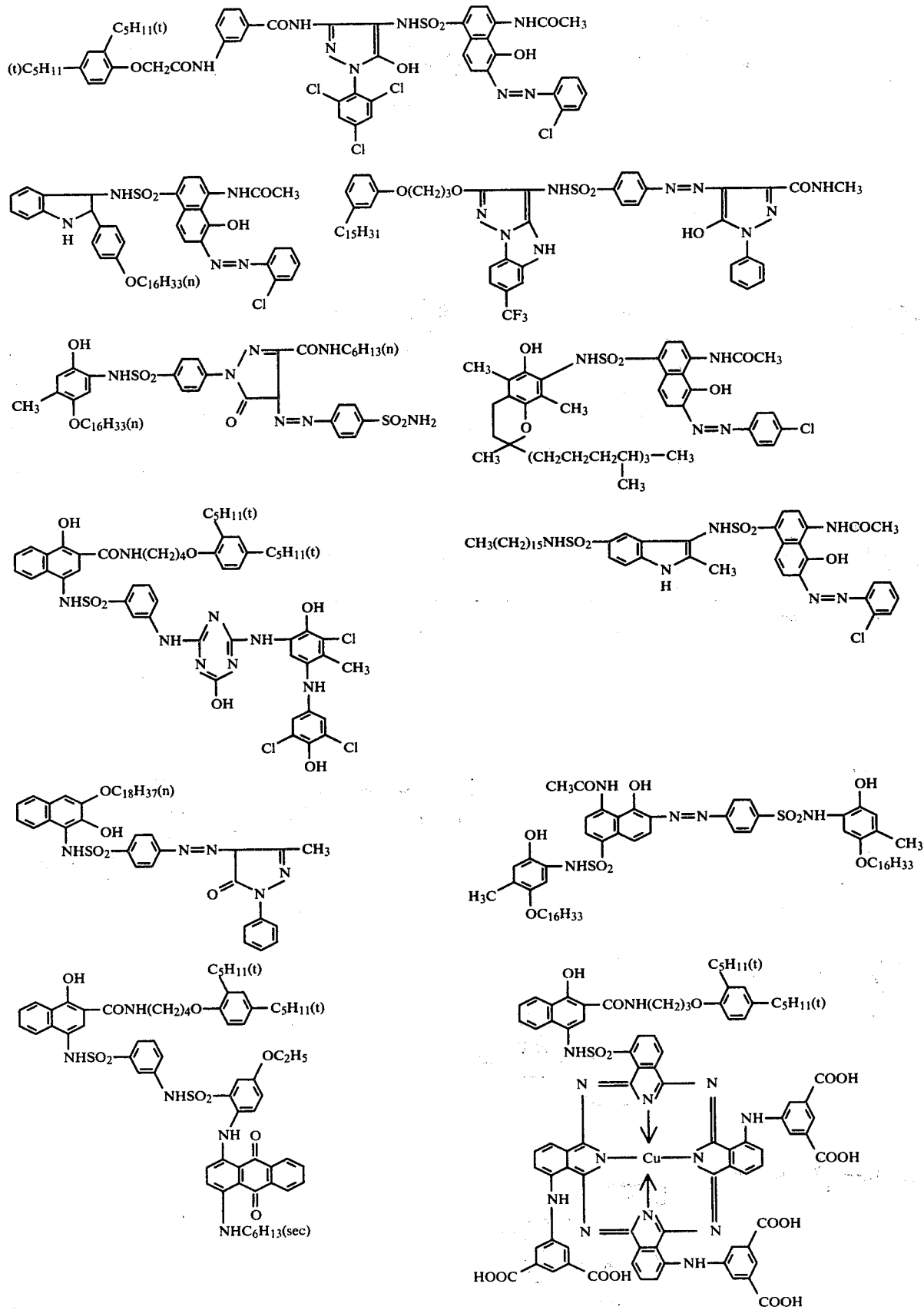

-continued
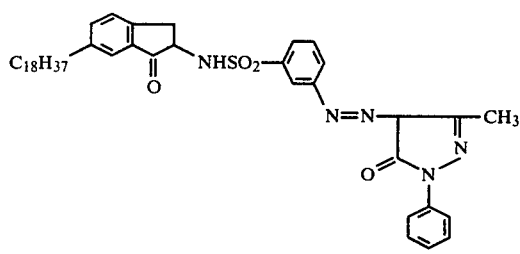
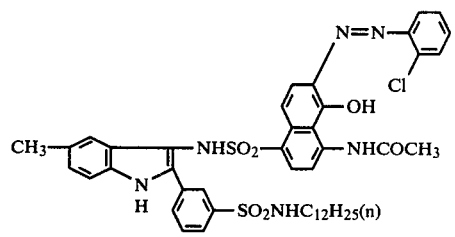
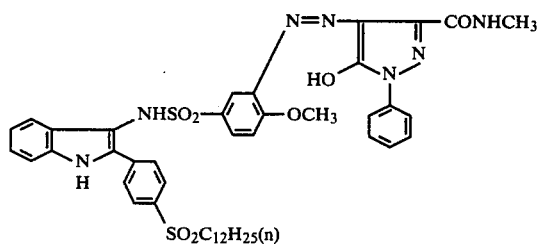
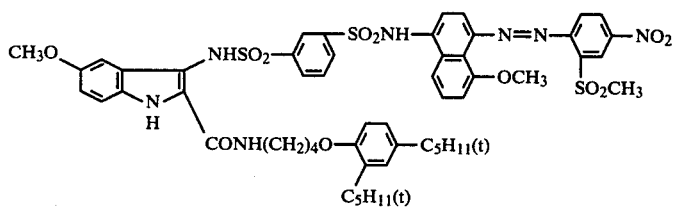
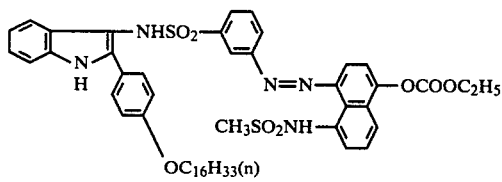
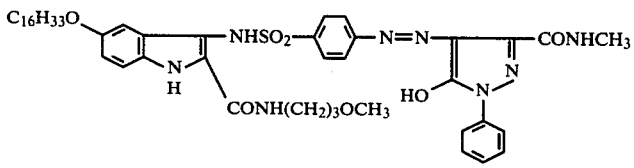
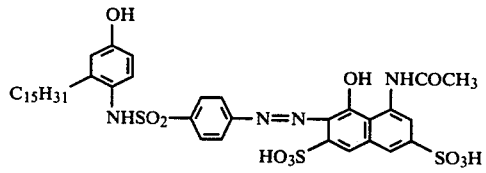
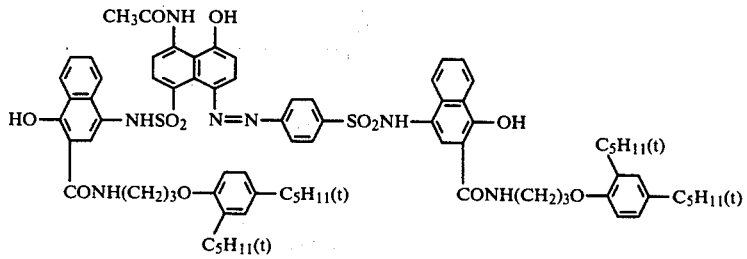

-continued
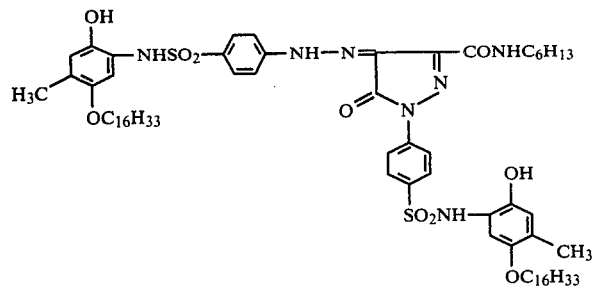
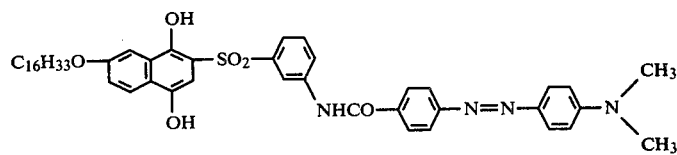
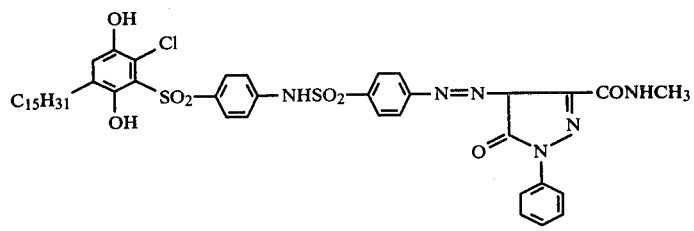
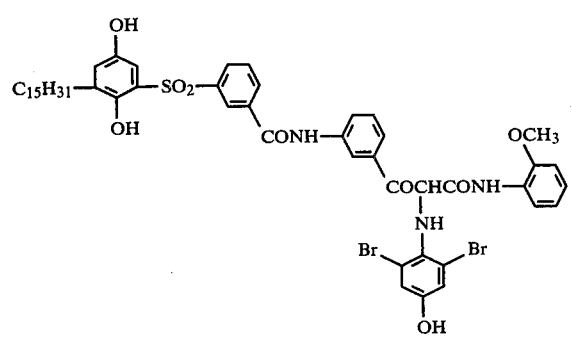
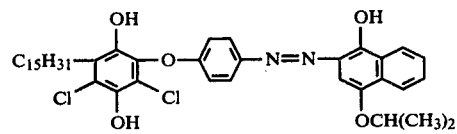
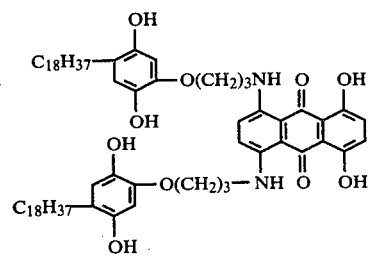
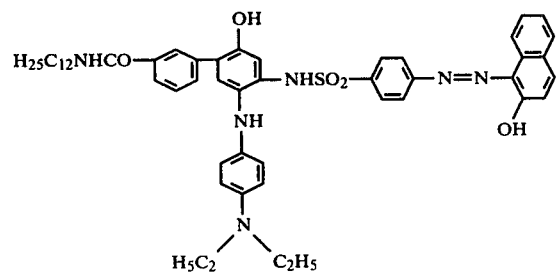
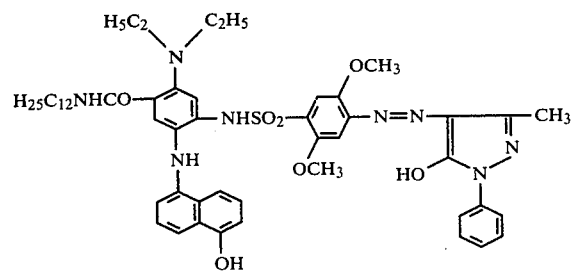
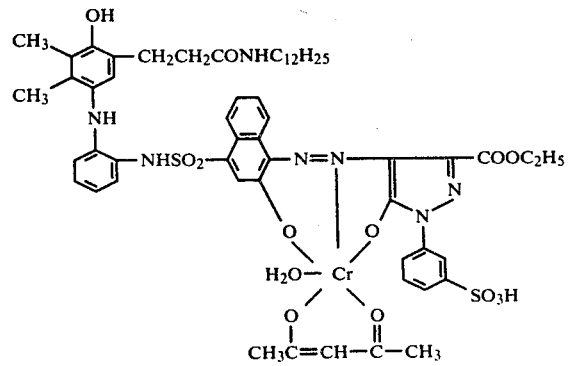

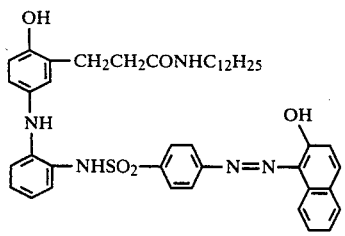

-continued

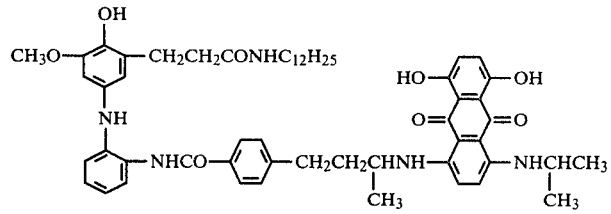

These image dye-forming substances can be dispersed in hydrophilic colloid according to a known method and can be added to a light-sensitive color photographic material. The above dispersion can be effected in a similar manner as that useful for dispersing the hydroquinone compounds and or precursors thereof according to the present invention. Further, utility for dispersing and adding said image dye-forming substance together with such hydroquinones as the hydroquinone compounds and or their precursors according to the present invention is also known. Alternatively, it is useful to use together two or more image dye-forming substances to a single light-sensitive silver halide emulsion, as described in Japanese CPI Patent Publication No. 54-48534/1979. For this, a single image dye-forming substance is usually used in a proportion of 15–85 mol%, preferably 20–80%, and more preferably in a proportion of 30–70% on the basis of the total value.

The amount of the image dye-forming substances associated with the light-sensitive silver halide emulsion can be widely varied depending upon the type of the image dye-forming substance used, the type of light-sensitive silver halide emulsion used, the process of development and effects desired. For example, the image dye-forming substance may be used in such amount that the mol ratio of the silver halide in the silver halide emulsion layer to said substance may be within the range of from about 0.5 to 50, preferably about from 5 to 5.

As the light-sensitive silver halide emulsion used in the light-sensitive color photographic material of this invention, an ordinary emulsion generally known which comprises a silver halide and a hydrophilic binder is useful and such emulsion is prepared and ripened by a known process. Further, to such silver halide emulsion, there may be added conventionally used additives, for example, a hardening agent, a natural sensitizer, a chemical stabilizer, a surface active agent, an antifoggant, a stabilizer, a sensitizing dye and supersensitization additive.

The above image dye-forming substances are used in combination with these light-sensitive silver halide emulsions. The image dye-forming substances can be included in the light-sensitive silver halide emulsion layer with which is associated and or in at least one layer other than said light-sensitive silver halide emulsion layer. Further, when two or more image dye-forming substances are used in combination these substances may be included either in the same layer or in separate layers.

Thus, by the association of the image dye-forming substance with the light-sensitive silver halide emulsion layer, image dye may be formed or a diffusible dye or a precursor thereof may be released as a function of the imagewise exposure through the reaction with the oxidation product of a silver halide developing agent.

The light-sensitive material of this invention can be used for various purposes, for example, as an ordinary color negative film, color positive film, color-printing-paper, color reversal film, etc. Furthermore, it can also conveniently by used as a light-sensitive material for color diffusion transfer process.

In particular, when the light-sensitive color photographic material of the present invention is used for color diffusion transfer process, it is generally desirable that a positive image is formed on an image-receiving layer. There are known various reversal processes for obtaining a positive, diffusion transfer dye image by using the image dye-forming substances belonging to the aforementioned group 2 or group 3.

For example, there can be used a process using a direct positive silver halide emulsion as described in U.S. Pat. No. 3,227,552, 2,592,250, 2,005,837, 3,367,778 and 3,761,276; British Pat. No. 1,011,062; Japanese Patent Publication No. 41-17184/1975; and Japanese OPI Patent Publication No. 50-8524/1975; a process using a physical development as described in British Patent 904,364 and Japanese OPI Patent Publication No. 47-325/1972 or a process which comprises adding a image dye-forming substance to a fogged emulsion layer and using as the adjacent layer a negative silver halide emulsion layer that contains such compound as releasing a development inhibiting agent as a result of reaction with the oxidation product of the silver halide developing agent as described in U.S. Pat. Nos. 3,227,554 and 3,632,345 and Japanese Patent Publication No. 43-21778/1968.

Thus, various processes can be used for obtaining positive dye images and preferably the above process comprising use of the direct positive silver halide emulsion is used. As the direct positive silver halide emulsion, for example, such silver halide emulsion is included that has been made possible to be developed on the whole surface by previous exposure or chemical treatment but becomes undevelopable imagewise by imagewise exposure.

As another direct positive silver halide emulsion, there is included such direct positive silver halide emulsion that as the light-sensitivity principally within the inside of silver halide particles. In the present invention, the latter direct positive silver halide emulsion as described in U.S. Pat. No. 2,761,276 is preferably used. When subjected to imagewise exposure, the direct positive silver halide emulsion forms a latent image principally within the inside of silver halide particles and when subjected to surface development under fog condition, it forms a positive silver image.

For such development processing under for condition, various processes are known. For example, so-called air fog developing solution as described in West German Pat. No. 850,383 or U.S. Pat. No. 2,497,875 may be used. Alternatively, on the development, the whole surface may be subjected to flash exposure, as described in West German Pat. No. 854,888; U.S. Pat. No. 2,592,298; British Pat. Nos. 1,150,553, 1,195,838 and 1,187,029. Further, the development process may be carried out in the presence of a fogging agent. As the fogging agent usable for this process, a hydrazine series compound and an N-substituted quaternary cycloammonium salt are included and these fogging agents can be used alone or together. Specifically, 1-[4-(2-formylhydrazino)-phenyl]-3-phenylthiourea and $\beta$-acetylphenylhydrazine are preferably used together with tert-butylamine borane as said fogging agent. Amount of the fogging agent can be varied widely depending upon the objects and, in general, when it is added to an alkaline processing composition, the amount is 0.1 to 2.0 g per liter of the alkaline processing composition and when it is added to a light-sensitive color photographic material, the amount is 0.001 to 10 g per $m^2$ of said material.

In the present invention, while various types of light-sensitive silver halide emulsions or various reversal processes can be used in combination with the image dye-forming substances, said image dye-forming substances should be placed in this case so that the sensitivity of the above light-sensitive silver halide emulsion may not be reduced thereby. That is to say, the image dye-forming substance which previously possesses the desired dye structure is desirably included in a layer located on the oppposite side to the light-sensitive silver halide emulsion layer with which said image dye-forming substance is to be combined, on the basis of the direction of exposure. To the contrary, in the case of a image dye-forming substance which possesses no dye structure on the exposure, such as an ordinary color forming coupler, a image dye-forming substance having short wavelength shift type dye, it is also possible to include such image dye-forming substances in the light-sensitive silver halide emulsion layer, because such image dye-forming substances do not reduce the sensitivity of the emulsion. Further, the image dye-forming substances can alternatively be included in a layer located to the direction of exposure with regard to said silver halide emulsion layer.

By the use of one or more sets of the unit comprising the light-sensitive silver halide emulsion layer and the image dye-forming substance, a monochrome or multicolor dye image can be obtained.

The light-sensitive wave length region of the light-sensitive silver halide emulsion layer and the absorption wave length region of the dye image formed by the image dye-forming substance associated with said emulsion layer may be the same or different and can be applied to so-called pseudocolor photography. When applied to ordinary multicolor photograph, a yellow image dye-forming substance is associated with a blue-sensitive emulsion layer, a magenta image dye-forming substance is associated with a green-sensitive emulsion layer and a cyan image dye-forming substance is associated with a red sensitive emulsion layer.

Further, two or more of these association units may be used by in a single layer, for example, as a so-called mixed packet emulsion.

The use of an inter-layer in the light-sensitive color photographic material of the invention is convenient. The inter-layer may not only prevent unpreferable interaction caused between different association units but also adjust the diffusibility of a diffusible dye or the precursor thereof or an alkaline processing composition. As a material for such inter-layer, gelatin, calcium alginate, vinyl acetatecrotonic acid copolymer, isopropyl cellulose, hydroxypropyl methyl cellulose, polyvinylamides, polyvinylamide graftcopolymer of a mixture of latex-liquid and a penetrating agent may be used. The above inter-layer may also be used as a filter layer by including therein colloidal silver or a filter dye. A protective layer may be set up as the outermost layer on the above-mentioned various layers on a support. As the protective layer, the similar material used in the inter-layer can be used.

On coating each of the above layers, it is convenient to use a coating aid in a coating composition in order to facilitate coating. Further, a viscosity increasing-agent may be added. As coating method, any of conventionally known methods may be employed. As the support of the light-sensitive color photographic material of this invention, one which is used in an ordinary light-sensitive photographic material can be used.

When the light-sensitive color photographic material of the invention is used as a photographic product for diffusion transfer process in which said material is kept under the integrated state after image-forming process, a vapor-permeable support is conveniently used in order to assist evaporation of water contained in the processing composition through the support. The support may be either transparent, opaque or translucent, depending on the purpose. For an opaque support, a pigment e.g. carbon black or titanium dioxide may be used if necessary, together with a suitable binder.

When the light-sensitive color photographic material of this invention is used in color diffusion transfer process which comprises a development process with an alkaline composition after the imagewise exposure, a diffusible dye or a precursor thereof which is released corresponding to a developed image diffuses up to an image-receiving layer and is subsequently fixed in the layer to form a image dye. The image-receiving layer used for these color diffusion transfer processes preferably contains a mordant.

As a suitable mordant for the image-receiving layer, any of those which have mordanting effect to the diffusible dye or its precursor, for example, poly-4-vinyl pyridine, poly-4-vinyl-N-benzylpyridinium-p-toluene sulfonate, cetyltrimethylammonium bromide, ter-copolymer of divinyl benzene, styrene and N,N-dimethyl-N-benzyl-N-p-(methacryloylaminophenyl)methylammonium chloride and such compounds as described in Japanese patent application No. 52-66494 may be used.

These mordants are used in combination with various dispersing agents such as ordinary gelatin, polyvinyl alcohol, polyvinyl pyrrolidone and completely or partially hydrolyzed cellulose ester and it is also possible for the image-receiving layer to be constituted singly with a dispersing agent which itself has a mordanting effect, e.g., poly-N-methyl-2-vinylpyridine, N-methoxy-methyl-poly-hexylmethyleneadipamide, copolymer of vinyl alcohol and N-vinylpyrrolidone or any mixture thereof, partially hydrolyzed polyvinyl acetate, acetyl cellulose, gelatin and polyvinyl alcohol. The mordant content in the image-receiving layer is preferably from 10 to 100% by weight.

Further, the mordant may be incorporated in a alkaline processing composition.

The image-receiving layer may contain a variety of additives used in an ordinary photography, such as UV absorber, optical whitening agent, etc.

When the substance which is to diffuse to the image-receiving layer is a dye precursor such as leuco dye, an oxidizing agent, a color developing agent or a diazonium compound may preferably be added to the image-receiving layer in order to convert said precursor into a dye.

It is necessary for the image-receiving layer to be superposed on a silver halide emulsion layer when the alkaline processing composition is effected, however, before or after the process these layers does not necessarily be superposed. After the image forming process the emulsion layer and the image-receiving layer may be kept together or split off.

The image-receiving layer may be coated either, as one of the constructive layers, on the same support of a light-sensitive material as described, for example, in U.S. Pat. Nos. 3,594,165 and 3,689,262 or coated on a separate support as described, for example, in U.S. Pat. Nos. 3,415,644 to 3,415,646. The image-receiving layer is usually formed on the separate support when the silver halide emulsion layer and the image-receiving layer are kept separate before the image forming process or when they are stripped off after the process.

As the support for the image-receiving layer a similar support used for the light-sensitive color photographic material may be used.

It is preferable that, after substantial formation of a dye image on the image-receiving layer is completed, PH values of both the silver halide emulsion layer and the image-receiving layer are preferably lowered to around neutral in order to increase the stability of the dye image formed and to substantially terminate more diffucion of image dye as well as to prevent discoloration or staining of image caused at high pH value. For this purpose, use of a neutralizing agent is preferable. As the material used as the neutralizing agent, a film-forming polymer acid containing one or more carboxyl group, sulfo group or such a group which forms a carboxyl group by the hydrolysis is preferable.

The polymer acid which may be used in the present invention preferably has molecular weight of about 10,000 to about 100,000 and, for example, monobutyl ester of 1:1 copolymer of maleic anhydride and ethylene; monobutyl ester of 1:1 copolymer of maleic anhydride and methyl vinyl ether; monoethyl ester, monopropyl ester, monopentyl ester and monohexyl ester of 1:1 copolymer of maleic anhydride and ethylene; monoethyl ester, monopropyl ester, monopentyl ester and monohexyl ester of 1:1 copolymer of maleic anhydride and methyl vinyl ether; polyacrylic acid; polymethacrylic acid; copolymers, at various ratios, of acrylic acid and methacrylic acid; copolymers, at various ratios, of acrylic acid or methacrylic acid and another vinyl series monomer, i.e., copolymers which contain at least 30 mol %, preferably 50-90 mol % of acrylic acid or methacrylic acid such as acrylic acid esters, methacrylic acid esters and vinyl ethers. In addition, metal salts as described in Research Disclosure 12331, a monomer acid, a ballasted organic acid, an alkyl phosphate, a polyacryl phosphate, poly(1-acryloyl-2,2,2-trimethylhydrazinium-p-toluenesulfonic acid salt) may also be used singly or, if necessary, together with a binder polymer. Further, if necessary, a polymer acid and a monomer acid, or a polymer acid and an organic amine may be used in combination. These polymer acid, monomer acid, organic amines and binder polymer are dissolved in, for example, alcohol, e.g., methanol, ethanol, propanol and butanol, ketones, e.g., acetone, methyl ethyl ketone, diethyl ketone and cyclohexanone, esters, e.g., methyl acetate, ethyl acetate, isopropyl acetate, butyl acetate or a mixture thereof and then applied. Furthermore, enmicrocapsulation is also possible.

Thickness of the neutralizing layer may be varied depending upon various factors such as the composition of the alkaline processing composition and the type or nature of the materials incorporated in the layer but generally 5–30μ is preferable.

Together with the above neutralizing layer, a timing layer (neutralization speed adjusting layer) for controlling fall of pH value may be applied. This timing layer will serve to delay pH fall until completion of desired image dye-formation and transfer. More specifically, the timing layer prevents undesirable fall of density in the transferred dye image, which is caused due to rapid pH fall within the system by the neutralizing layer.

As a material used for the timing layer, various materials can be used e.g., gelatin, polyvinyl alcohol, partial acetallized polyvinyl alcohol, partially hydrolyzed polyvinyl acetate, cyanoethylated polyvinyl alcohol, hydroxypropyl methyl cellulose, diacetyl cellulose, isopropyl cellulose, polyvinylamides, polyvinylamide graftcopolymer or a combination of latex liquid and a penetrating agent is useful.

The above neutralizing layer and the timing layer may be conted either on the support for a light-sensitive color photographic material or on a separate support together with on image-receiving layer. They may also be coated as a constructive layer on a support for a processing sheet as referred to hereinlater.

When an image-receiving layer is coated on the same support for a light-sensitive color photographic material before it is subjected to the image-forming process and peeling off after the process from said light-sensitive photographic material, use of a stripping layer is preferable. As a stripping layer, for example, those described in U.S. Pat. No. 3,730,718 may be used.

When the light-sensitive color photographic material of this invention is used as a print paper in color diffusion transfer process or as an conventional color print paper, an optical reflection layer having high whiteness is applied on the opposite side of an image dye-forming layer with respect to the direction of observation. Said image dye-forming layer is in the case of color diffusion transfer process an image-receiving layer and, in the case of ordinary color print paper, it generally means an image dye-forming substance containing layer. The optical reflection layer may be incorporated in a support or as an independent layer in advance. Alternatively in the color diffusion transfer process, an optical reflection agent may be incorporated in the alkaline processing composition so that the optical reflection layer may be formed during the image-forming step. The same purpose will be obtained by a support having higher optical reflectance by containing a photoreflective agent.

As the optical reflection agent, for example, titanium dioxide, zinc oxide, barium sulfate, silver in flake form, alumina, barium stearate or zirconium oxide can be used either singly or in combination. When the optical reflection agent is applied in advance as a layer, it may be dispersed in any hydrophilic binder such as gelatin or polyvinyl alcohol through which the alkaline processing composition can penetrate.

To the above optical reflection layer, a brightening agent like stilbene series compounds, coumarin series compounds or phenylaminotriazine series compounds may also be added.

The light-sensitive photographic materials used for color diffusion transfer process are often used for so-called instant photography in which the material is processed immediately after exposure. When the development of the silver halide emulsion is carried out after exposure in a light place, an opacifying layer is preferably applied in order to prevent the silver halide emulsion from being further exposed to light. Such opacifying layer may be applied as a layer in the light-sensitive color photographic material in advance or may be provided during the image-forming process. As an opacifying agent, carbon black or an indicator dye may be added. It is also convenient to use a desensitizing agent.

The above optical reflection layer and the opacifying layer may exist either as the same layer or as separate layers adjacent to each other.

The light-sensitive color photographic material of this invention may be processed according to any ordinary known procedures after exposure. The known procedures include color development, bleaching and fixing or bleach-fixing, washing stabilization and, if necessary, pre-hardening, neutralization, stopping and black-and-white development (for example, the first development in the reversal process) may be effected.

The light-sensitive color photographic materials of this invention can also be processed according to conventionally known color diffusion transfer processes. For example, the light-sensitive material of this invention is, after the imagewise exposure, immersed in an alkaline processing composition or contacted with said composition and thereby diffusible dye or its precursor is released. The alkaline processing composition used here is a liquid composition containing processing components necessary for the development of the silver halide emulsion and for the formation of diffusion transfer image. The solvent used for this alkaline processing composition consists mainly of water but a hydrophilic solvent such as acetone or methyl cellosolve may also be used additionally. The above alkaline processing composition contains necessary amount of alkali agent for the development of the silver halide emulsion and for the dye image formation. As said alkali agent, sodium hydroxide, potassium hydroxide, calcium hydroxide, tetramethylammonium hydroxide, sodium carbonate, sodium phosphate or diethylamine can be mentioned. The alkaline processing composition preferably possesses a pH value of about 9 or more at room temperature. With this alkaline processing composition, the required alkaline condition which is preferably $10^{-5}$ to 2 mols of hydroxidion concentration per liter is achieved. The alkaline processing composition may contain a viscosity increasing agent, for example, a high molecular viscosity increasing agent which is inert to the alkali solution, such as hydroxyethyl cellulose, carboxymethyl hydroxyethyl cellulose, sodium carboxymethyl cellulose, hydroxypropyl cellulose. The concentration of the viscosity increasing agent is preferably from 1 to 10% by weight of the alkaline processing composition, whereby the viscosity of said alkaline processing composition is kept at about 100 to 300,000 centipoise and the distribution of the alkaline processing composition during the image-forming process can be made homogeneous. Further, the viscosity increasing agent possesses such effect as preventing the undesirable change of image after substantial formation of a dye image, by forming non-flowable film during image-forming process. It is preferable that said alkaline processing composition contains a silver halide developing agent, and it may further contain a benzotriazole type compound, e.g., 5-methylbenzotriazole; a benzimidazole series compound, e.g., 5-nitrobenzimidazole; a tetrazaindene series compound, e.g., 4-hydroxy-5,6-cyclopenteno-1,3,3a,7-tetrazaindene; sulfite or potassium bromide. Also, a fogging agent or a solvent for silver halide may be added to said processing composition in accordance with the type of the silver halide emulsion employed.

The alkaline processing composition may preferably be kept in a ruptuable pod. For example, it is desirably kept in a hollow pod which has been formed by folding a sheet, said sheet being made of liquid and air-permeable material, and sealing each end side, so that the pod can be broken at a predetermined portion by the internal pressure applied to the alkaline processing composition, when the pod passes through the pressure devices, releasing thereby the alkaline processing composition.

As the material forming the above pod, such material as a laminate of polyethylene terephthalate/polyvinyl alcohol/polyethylene or a laminate of lead foil/vinyl chloridevinyl acetate copolymer is conveniently used. The pod is preferably fixed along the leading edge of the light-sensitive photographic material so that the composition kept therein may be spread out over the surface of the light-sensitive photographic material substantially in one direction.

The developing agent used for the light-sensitive color photographic material of the invention, includes known 3-pyrazolidone compounds, hydroquinone compounds, catechol compounds, aminophenol compounds and p-phenylenediamine compounds. Preferably p-phenylenediamine compounds may be employed when an image dye-forming substance is selected from aforementioned group 1 or 2. On the other hand when the image dye-forming substance is selected from group 3,3-pyrazolidone compounds may be preferable in view of less stain caused by this type of compound.

Furthermore, as described in Japanese OPI Patent Publication No. 51-111334/1976, two or more silver halide developing agents can be used together.

The silver halide developing agent is usually incorporated according to any known manner in an alkaline processing composition or a developing solution, it is also possible for said developing agent to be incorporated in at least one of the layers of the light-sensitive color photographic material in advance. Further, it can be incorporated both in the alkaline processing composition and the light-sensitive color photographic material. When the above silver halide developing agent is incorporated in the light-sensitive color photographic material in advance, it may be applied in the form of precursor.

Layers to which said developing agent can be incorporated include, for example, the silver halide emulsion layer, image dye-forming substance-containing layer, interlayer, protective layer, etc.

The light-sensitive color photographic materials of this invention can conveniently be used as the light-sensitive photographic material for various types of color diffusion transfer process.

The photographic product for color diffusion transfer process usually comprises two supports and a light-sensitive silver halide emulsion layer, an image dye-forming substance and an image-receiving layer which layers are so arranged as to be present between the supports during image-forming process.

In the case where the image-receiving layer is coated before the image-forming process on the same support for the light-sensitive color photographic material as one of the constructive layers, a processing sheet is preferably used in order to distribute the alkaline treating composition homogeneously and enable good diffusion.

As the processing sheet, a similar material as used for the support of the light-sensitive color photographic material can optionally be employed depending upon purposes. The sheet may be either transparent or opaque depending upon the purpose. Further, the processing sheet may comprise as a constructive layer, a layer containing a mordant, a neutralizing layer and timing layer.

The photographic products for color diffusion transfer process, when used as so-called instant photographic, usually contain an alkaline processing composition and means for applying said processing composition to the light-sensitive photographic material. As such photographic products, any one of those described, for example, in U.S. Pat. Nos. 3,415,644, 3,415,645, 3,415,646, 3,473,925, 3,573,042, 3,573,043, 3,594,164, 3,594,165, 3,615,421, 3,576,626, 3,658,524, 3,635,707, 3,672,890, 3,730,718, 3,701,656 and 3,689,262; Japanese OPI Patent Publication No. 50-6337; Belgian Patent Nos. 757,959 and 757,860 may be applied to the present invention.

The present invention will be illustrated in more detail by the following Examples.

EXAMPLE 1

On a transparent polyethylene terephthalate film support having 150 μm in thickness, the following layers were coated successively to prepare an integrated monocolor photographic element:

(1) Image-receiving layer having 4 μm in dry thickness containing ter-copolymer of styrene,N-vinylbenzyl-N-benzyl-N,N-dimethylammonium chloride and divinylbenzene (in molar ratio of 49/49/2) (22 mg/100 cm$^2$) and gelatin (22 mg/100 cm$^2$), (2) Optical reflection layer having 9 μm in dry thickness containing titanium dioxide (230 mg/100 cm$^2$) and gelatin (22 mg/100 cm$^2$), (3) Black opacifying layer having 5 μm in dry thickness containing carbon black (25 mg/100 cm$^2$) and gelatin (17 mg/100 cm$^2$), (4) Magenta image dye-forming substance-containing layer having 2 μm in dry thickness containing magenta DRR compound A (8 mg/100 cm$^2$), N,N-dietyl lauramide (11 mg/100 cm$^2$), (5) Layer containing gelatin (24 mg/100 cm$^2$) and (6) Light-sensitive silver halide emulsion layer having 2.5 μm in dry thickness containing negative type silver iodobromide emulsion (1.6 mol % of silver iodide, 15.0 mg/100 cm$^2$ when calculated in terms of silver), mucochloric acid (1.3 mg/100 cm$^2$) and gelatin (24 mg/100 Cm$^2$).

The photographic element thus prepared was used as a standard and further a light-sensitive elements according to the present invention and for comparison were prepared according to the following procedures:

In the above standard light-sensitive material, the following layer (7) was applied in place of the layer (5):

(7) Layer containing a hydroquinone compound according to the present invention and a comparative compound (6×10$^{-6}$ mol/100 cm$^2$ and 12×10$^{-6}$ mol/100 cm$^2$), dibutyl phthalate (½ by weight of the above hydroquinone compound and gelatin (24 mg/100 cm$^2$).

Then, on a transparent polyethylene terephthalate film support having 100 μm in thickness, the following layers were coated successively to prepare a processing sheet:

(1) Neutralizing layer having 17 μm in dry thickness containing copolymer of acrylic acid and butyl acrylate (in the weight ratio of 70/30) (200 mg/100 cm$^2$) and (2) Timing layer having 4.5 μm in dry thickness containing cellulose diacetate (55 mol % of acetylation (57 mg/100 cm$^2$).

Each of the integrated monocolor photographic elements thus prepared was subjected to a predetermined exposure through an optical wedge comprising in total 30 different density steps of silver with the density difference between each two steps being 0.15 and after the above processing sheet was superposed on to the element, a pod having the content of 1.0 ml and containing on alkaline processing composition having the following composition was applied between the element and the processing sheet. A sample thus prepared was passed through a pair of rollers parallely located at the distance of 340 μm and under pressure to rupture the pods and spread the alkaline processing composition between the light-sensitive silver halide emulsion layer (6) and the timing layer of the processing sheet.

The composition of the alkaline processing composition was as follows:

| | |
|---|---|
| Potassium hydroxide | 56g |
| Sodium sulfite | 2.0g |
| 4-Hydroxymethyl-4-methyl-1-phenyl-3-pyrazolidone | 8.4g |
| 5-Methylbenzotriazole | 2.8g |
| 2-Tert-butylhydroquinone | 0.3g |
| Carbon black (Raven-450; manufactured by Columbian Carbon) | 160g |
| Carboxy methyl cellusone sodium salt (high viscosity type; manufactured by Tokyo Kasei) | 60.0g |
| Benzyl alcohol | 1.5ml |
| Distilled water to make up | 1000.0ml |

After the above treatments, each sample was allowed to stand at room temperature for 2 hours and thereafter the reflection density of the image formed on the image-receiving layer was measured with Sakura Photoelectric densitometer PDA-60 (manufactured by Konishiroku Photo Industry) by using green filter. Then the characteristic curves were drawn with respect to each sample.

Scavenging ability of the hydroquinone compound according to the present invention and for comparison was estimated according to the following equation:

$$\psi^H = \frac{D_{0.4}^H - 0.4}{\Delta D_{BL}} \times 100$$

wherein $\Delta D_{BL}$ represents the difference between the maximum density ($D_{max}$) and the minimum density ($D_{min}$) of the standard sample ($\Delta D_{BL} = D_{max} - D_{min}$) and $D_{0.4}^H$ represents the density value of the standard sample at the exposure where a sample containing the hydroquinone compound gives density 0.4.

Scavenging abilities thus estimated of the hydroquinone compounds according to the present invention and for comparison are shown in Table 1.

The Scavenging ability ψ means the degree of ability of the hydroquinone compound to inactivate the oxidation product of a silver halide developing agent, and thus to inhibit the reaction between said oxidation product and a dye image-forming substance. Therefore the greater the value of ψ is the stronger is the scavenging ability. It will be clearly understood from the results shown in Table 1 that the hydroquinone compounds according to the present invention have higher scavenging ability than the comparative compounds.

TABLE 1

| Sample No. | Compound | Amount Coated ($10^{-6}$ mol/100 cm$^2$) 6 | 12 |
|---|---|---|---|
| | | Scavenging ability $\psi^H$ | |
| 1-1 | Hydroquinone compound according to this invention (1) | 69 | 86 |
| 1-2 | Hydroquinone compound according to this invention (2) | 69 | 90 |
| 1-3 | Hydroquinone compound according to this invention (3) | 65 | 84 |
| 1-4 | Hydroquinone compound according to this invention (13) | 68 | 84 |
| 1-5 | Hydroquinone compound according to this invention (15) | 66 | 90 |
| 1-6 | Hydroquinone compound according to this invention (16) | 66 | 91 |
| 1-7 | Hydroquinone compound according to this invention (17) | 67 | 90 |
| 1-8 | Comparison compound I | 40 | 60 |
| 1-9 | Comparison compound II | 25 | 45 |
| 1-10 | Comparison compound III | 40 | 65 |
| 1-11 | Comparison compound IV | 42 | 63 |

EXAMPLE 2

In a similar manner as in Example 1 except that the following layer (8) was coated in place of the layers (5) and (6) of the standard light-sensitive material of Example 1, another standard light-sensitive material 2-1 was prepared: (8) Light-sensitive silver halide emulsion layer having 2 μm in dry thickness containing green sensitive direct positive silver bromide emulsion having high internal sensitivity and low sensitivity (14.0 mg/100 cm$^2$ calculated in terms of silver), 2-sec-octadecylhydroquinone-5-sulfonic acid potassium salt (1.0 mg. 100 cm$^2$), 1-acetyl-2-[p-{5-amino 2-(2,4-di-tert-amylphnoxy)-benzamido}phenyl]hydrazine (0.2 mg/100 cm$^2$), mucochloric acid (1.0 mg/100 cm$^2$) and gelatin (17.0 mg/100 cm$^2$).

The said direct positive emulsion is such type of emulsion as described in U.S. Pat. No. 3,761,276.

Then, comparative light-sensitive materials 2-2 to 2-4 and the light-sensitive materials of this invention 2-5 to 2-7 were prepared in a similar manner, except that together with the magenta DRR compound A to be added to the layer (4) of the standard light-sensitive material 2-1, a comparison compound or a hydroquinone compound according to this invention, dissolved in the solvent (N,N-diethyllauramide) and dispersed in gelatin, respectively, was added to the above layer (4). The amount of the magenta DDR compound A coated was adjusted so that it may be equal to that in the light-sensitive material 2-1. Further, the amounts of the comparison compound and the hydroquinone compound according to the present invention were 3 mol % of the magenta DDR compound A.

In a similar manner as in Example 1, these light-sensitive materials thus prepared was subjected to exposure and then processed after being combined with the processing sheet and the pods containing the alkaline processing composition, as used in Example 1. After two hours from the completion of the image-forming process, the magenta dye image formed on the image-receiving layer was measured through a green filter. Results obtained are shown in Table 2, wherein $D_{max}$ and $D_{min}$ represent the maximum density and the minimum density, respectively. Relative speed is shown in terms of a logarithm of the amount of exposure required to obtain density of 0.5 and the difference form that obtained from the standard sample (Δ log E) was given here.

TABLE 2

| Light-sensitive material | Compound | $D_{min}$ | $D_{max}$ | Relative speed |
|---|---|---|---|---|
| 2-1 | No compound added | 0.32 | 2.03 | 0.00 |
| 2-2 | Comparison compound I | 0.28 | 2.01 | 0.05 |
| 2-3 | Comparison compound III | 0.26 | 1.95 | 0.10 |
| 2-4 | Comparison compound V | 0.26 | 2.00 | 0.03 |
| 2-5 | Hydroquinone compound according to this invention (1) | 0.21 | 2.02 | 0.10 |
| 2-6 | Hydroquinone (2) compound according to this invention | 0.23 | 1.93 | 0.12 |
| 2-7 | Hydroquinone (13) compound according to this invention | 0.22 | 1.99 | 0.06 |

As shown in Table 2 above, in comparison with the samples containing comparison compounds, the samples containing the hydroquinone compounds according to this invention have lower $D_{min}$ values and thus are more excellent in the anti-color fog effect. Further, it appears that the above hydroquinone compounds show neither fall of $D_{max}$ nor desensitization. Thus, it would be understood that the excellent scavenging ability of the hydroquinone compounds according to the present invention as shown in Example 1 brings about such effect as satisfactorily controlling $D_{min}$ of dye image.

EXAMPLE 3

On a polyethylene terephthalate support having about 100 μm in thickness, the following layers were coated successively to prepare an integrated dicolor photographic element:

(1) Black opacifying layer having 7 μm in dry thickness containing carbon black (35 mg/100 cm$^2$) and gelatin (24 mg/100 cm$^2$).

(2) Light-sensitive silver halide emulsion layer having 2 μm in dry thickness containing red-sensitive, direct positive silver bromide emulsion having high internal sensitivity (14.0 mg/100 cm$^2$ calculated in terms of silver), 2-sec-octadecyl-hydroquinone-5-sulfonic acid potassium salt (1.0 mg/100 cm$^2$), 1-acetyl-2-[p-{5-amino-2-(2,4,-di-tert-amylphenoxy)benzamido}phenyl]hydrazine (0.2 mg/100 cm$^2$), cyan DDR coupler B (8.0 mg/100 cm$^2$), N,N-diethyl lauramide (5.0 mg/100 cm$^2$), a hydroquinone compound according to this invention or for comparison ($8.5 \times 10^{-7}$ mol/10 cm$^2$) and gelatin (15.0 mg/100 cm$^2$), (3) Inter-layer having 1.5 μm in dry thickness containing a hydroquinone compound according to this invention or for comparison ($1.2 \times 10^{-5}$ mol/100 cm$^2$), dibutyl phthalate (3 mg/100 cm$^2$) and gelatin (15 mg/100 cm$^2$), (4) Light-sensitive silver halide emulsion layer having 2 μm in dry thickness containing green light-sensitive direct positive silver bromide emulsion having high internal sensitivity (14.0 mg/100 cm$^2$ calculated in terms of silver), 2-sec-octadecylhydroquinone-5-sulfonic acid potassium salt (1.0 mg/100 cm$^2$), 1-acetyl-2-[p-{5-amino-2-(2,4-di-tert-amylphenoxy)benzamido}-phenyl]hydrazine (0.2 mg/100 cm$^2$), magenta DDR coupler C (6.0 mg/100 cm$^2$), N,N-diethyl lauramide (4.0 mg/100 cm$^2$), a hydroquinone compound according to this invention or for comparison ($9 \times 10^{-7}$ mol/100 cm$^2$) and gelatin (15.0 mg/100 cm$^2$) and (5) Protective layer having 1.0 μm in dry thickness containing N,N',N"-tri-acryloyl-hexahydro-s-triazine (4.0 mg/100 cm$^2$), a hydroquinone compound according to this invention or for comparison ($1.2 \times 10^{-5}$ mol/100 cm$^2$), dibutyl phthalate (3 mg/100 cm$^2$) and gelatin (11.0 mg/100 cm$^2$).

Then, on a transparent polyethylene terephthalate film support having 100 μm thickness, the following layers were coated successively to prepare an image-receiving element having a image-receiving layer:

(1) Neutralizing layer having 20.0 μm in dry thickness containing partially butyl esterified product of a copolymer of polyethylene and maleic anhydride (200 mg/100 cm$^2$), (2) Timing layer having 6.0 μm in dry thickness containing a copolymer of butyl acrylate, diacetone acrylamide, styrene and methacrylic acid (in molar ratio of 60/30/4/6) and polyacrylamide (60 mg/100 cm$^2$) and (3) Image-receiving layer having 3 μm in dry thickness containing poly-4-vinyl pyridine (10 mg/100 cm$^2$) and polyvinyl alcohol (20 mg/100 cm$^2$).

The integrated dicolor photographic elements thus prepared were subjected to an ordinary exposure for sensitometry and to such exposures according to the processes given below (process b and process c) for observing olor separation of the samples.

Process a:

A similar exposure as in Example. 1.

Process B.

[The exposure (b-1) is followed by the expossure (b-2) as given below.]

(b-1): Overal uniform exposure on the whole surface through a red interference filter (maximum transmission wave length $\lambda_{max}$=646 nm, KL-65: manufactured by Tokyo Shibaura Denki) so as to achieve the red density of 0.3.

(b-2): Imagewise exposure using the same optical wedge as used in the above process a.

Process c:

[The exposure (c-1) is followed by the exposure (c-2) as given below.]

(c-1): Similar overall uniform exposure as in (b-1), except that, in place of the above red filter, a green filter ($\lambda_{max}$=548 nm, KL-55; manufactured by Tokyo Shibaura Denki) was used so as to achieve the green density of 0.3.

(c-2): The same exposure as (b-2).

Each of the sample elements which were subjected to exposure was processed in a similar manner as in Example 1 after being combined with the image-receiving element and the alkaline processing composition having the composition given herein below. After being allowed to stand at room temperature for 2 hours, reflection densities of the samples were determined by means of the afore-mentioned densitometer using a red filter ($\lambda_{max}$=644 nm) and a green filter ($\lambda_{max}$=540 nm).

With respect to the samples which were subjected to exposure according to the process a, the characteristic curves were obtained according to an ordinary method.

Degree of color separation of the samples which were subjected to exposure according to the processes b and c were evaluated according to the following method:

For each step, red reflection density and green reflection density were plotted, plotting red density ($D^R$) against green density ($D^G$) for the samples treated according to the process b and plotting green density ($D^G$) against red density ($D^R$) for the samples treated according to the process c. From the gradient at the straight line portion in each graph ($D^R/D^G$, $D^G/D^R$), so-called tri-chromatic coefficients ($\alpha^M$, $\alpha^C$) were obtained.

As monocolor samples, those wherein the layers (3) and (4) or (2) and (3) of the above-defined light-sensitive material are excluded were prepared and indicated as cyan monocolor light-sensitive material 3-8 and magenta monocolor light-sensitive material 3-7, respectively. The above light-sensitive material 3-8 was subjected to the exposure according to the above processes a and c and the light-sensitive material 3-7 was subjected to the exposure according to the above processes a and b and these samples were processed and measured in a similar manner as for the light-sensitive material 3-1. The alkaline processing composition used in this Example had the following composition:

| Potassium hydroxide | 40.0 g |
|---|---|
| Piperidino hexose reductone | 0.8 g |
| Sodium sulfite | 3.0 g |
| 3-Methoxy-4-amino-N-ethyl-N-β-hydroxyethyl-p-phenylenediamine | 35 g |
| 5-Methylbenzotriazole | 2.0 g |
| Benzyl alcohol | 10 ml |
| Carboxy methyl cellulose sodium salt | 60 g |
| Titanium dioxide | 500 g |
| Water to make up | 1 liter |

The results are given below in Table 3.

TABLE 3

| Light-sensitive material | Compounds Layers (2) to (5) being common | Process for exposure | | | |
|---|---|---|---|---|---|
| | | Process a | | Process b | Process c |
| | | $D_{min}^G$ | $D_{min}^G$ | $\alpha^M$ | $\alpha^C$ |
| 3-1 | Comparison compound I | 0.35 | 0.31 | 0.12 | 0.24 |
| 3-2 | Comparison compound III | 0.34 | 0.33 | 0.14 | 0.24 |
| 3-3 | Comparison compound IV | 0.32 | 0.30 | 0.15 | 0.23 |
| 3-4 | Hydroquinone compound according to this invention | 0.24 | 0.25 | 0.11 | 0.18 |

TABLE 3-continued

| Light-sensitive material | Compounds Layers (2) to (5) being common | Process for exposure | | | |
|---|---|---|---|---|---|
| | | Process a $D_{min}^G$ | Process b $D_{min}^G$ | Process b $\alpha^M$ | Process c $\alpha^C$ |
| 3-5 | (1) Hydroquinone compound according to this invention | 0.25 | 0.23 | 0.13 | 0.19 |
| 3-6 | (13) Hydroquinone compound according to this invention | 0.26 | 0.24 | 0.12 | 0.18 |
| 3-7 | (15) Hydroquinone compound according to this invention (1) (magenta monochrome) | 0.25 | — | 0.11 | — |
| 3-8 | (magenta monochrome) (1) (Cyan monochrome) | — | 0.24 | — | 0.19 |

In the Table 3, $\alpha^M$ and $\alpha^C$ values indicate that the closer the values to those of the standard light-sensitive materials 3-7 and 3-8, respectively, the higher is the degree of color separation. Thus, it is apparent that the samples containing the hydroquinone compounds of the present invention give better results compared with the comparison samples.

EXAMPLE 4

On a transparent polyethylene terephthalate film support having 150 μm in thickness, the following layers were coated successively to prepare integrated multicolor photographic elements 4-1 (comparative light-sensitive material) and 4-2 (light-sensitive material of this invention) for color diffusion transfer process:

Element 4-1

(1) Image-receiving layer having 4 μm in dry thickness containing ter-copolymer of divinyl benzene, styrene and N,N-dimethyl-N-benzyl-N-p-(methacryloylaminophenyl)-methylammonium chloride (in the molar ratio of 4/48/48) (22 mg/100 cm$^2$) and optical whitening agent (0.4 mg/100 cm$^2$), (2) Optical reflection layer having 9 μm in dry thickness containing titanium dioxide (230 mg/100 cm$^2$) and gelatin (22 mg/100 cm$^2$), (3) Black opacifying layer having 5 μm in dry thickness containing carbon black (25 mg/100 cm$^2$) and gelatin (17 mg/100 cm$^2$), (4) Cyan dye image-forming substance containing layer having 2 μm in dry thickness, which contains cyan DRR compound D (6 mg/100 cm$^2$), N,N-diethyl lauramide (11 mg/100 cm$^2$), the comparison compound III (0.1 mg/100 cm$^2$) and gelatin (17 mg/100 cm$^2$), (5) Light-sensitive silver halide emulsion layer having 1.5 μm in dry thickness containing red sensitive direct positive silver bromide emulsion having high internal sensitivity (14.0 mg/100 cm$^2$ calculated in terms of silver), 2-sec-octadecylhydroquinone-5-sulfonic acid potassium salt (1.0 mg/100 cm$^2$), 1-acetyl-2-[p-{5-amino-2-(2,4-di-tert-amulphenoxy)benzamido}-phenyl]hydrazine (0.2 mg/100 cm$^2$) and gelatin (16.5 mg/100 cm$^2$), (6) Inter-layer having 1.5 μm in dry thickness containing the comparison compound III (6.0 mg/100 cm$^2$), dibutyl phthalate (3 mg/100 cm$^2$) and gelatin (15 mg/100 cm$^2$), (7) Magenta dye image-forming substance containing layer having 2 μm in dry thickness, which contains magenta DRR compound A (7.0 mg/100 cm$^2$), N,N-diethyl lauramide (11.0 mg/100 cm$^2$), the comparison compound III (0.15 mg/100 cm$^2$) and gelatin (17 mg/100 cm$^2$), (8) Light-sensitive silver halide emulsion layer having 1.5 μm in dry thickness, containing green sensitive direct positive silver bromide emulsion having high internal sensitivity (14.0 mg/100 cm$^2$, calculated in terms of silver), 2-sec-octadecylhydroquinone-5-sulfonic acid potassium salt (1.0 mg/100 cm$^2$), 1-acetyl-2-[p-{5-amino-2-(2,4-di-tert-amylphenoxy)benzamido}-phenyl]hydrazine (0.2 mg/100 cm$^2$) and gelatin (17.0 mg/100 cm$^2$), (9) Inter-layer having 1.5 μm in dry thickness containing comparison compound III (6.2 mg/100 cm$^2$), dibutyl phthalate (3 mg/100 cm$^2$) and gelatin (15 mg/100 cm$^2$),

(10) Yellow dye image-forming substance containing layer having 2 μm in dry thickness, which contains yellow DRR compound E (10 mg/100 cm$^2$), N,N-diethyl lauramide (18 mg/100 cm$^2$), comparison compound III (0.4 mg/100 cm$^2$) and gelatin (17 mg/100 cm$^2$),

(11) Light-sensitive silver halide emulsion layer having 1.6 μm in dry thickness blue sensitive direct positive silver bromide emulsion having high internal sensitivity (14.0 mg/100 cm$^2$, calculated in terms of silver), 2-sec-octadecylhydroquinone-5-sulfonic acid potassium salt (1.0 mg/100 cm$^2$), 1-acetyl-2-[p-{5-amino-2-(2,4-di-tert-amylphenoxy)benzamido}phenyl]hydrazine (0.2 mg/100 cm$^2$) and gelatin (10.5 mg/100 cm$^2$) and

(12) Protective layer having 1.0 μm in dry thickness containing tetrakis (vinylsulfonylmethyl) methane (0.8 mg/100 cm$^2$), comparison compound III (4 mg/100 cm$^2$), dibutyl phthalate (2 mg/100 cm$^2$) and gelatin (10.0 mg/100 cm$^2$).

Element 4-2

This element was prepared in a similar manner as the Element 4-1, except that the comparison compound III as used in the layers (4), (6), (7), (9), (10) and (12) of the above Element 4-1 was replaced with the hydroquinone compound (1) according to the present invention. The amount of the above hydroquinone compound coated was the equimolar amount as the comparison compound III in the Element 4-1.

Element 4-3

An integrated cyan monocolor photographic element comprising the layers (1) to (5) of the above Element 4-2 was prepared and used as a standard for the estimation of color separation.

Element 4-4

An integrated magenta monocolor photographic element was prepared by coating on an element which comprises the layers (1) to (3) of the above Element 4-2, the layers (7) and (8) of the Element 4-2 and used as a standard for the estimation of color separation.

Element 4-5

An integrated yellow monocolor photographic element was prepared by coating on an element which comprises the layers (1) to (3) of the Element 4-2, the layers (10) and (11) of the Element 4-2 and used as a standard for the estimation of color separation.

Subsequently, on a transparent polyethylene terephthalate film support having 100 μm in thickness, the following layers were coated successively to prepare a processing sheet.

(1) Neutralizing layer having 17 μm in dry thickness containing copolymer of acrylic acid and butyl acrylate (in the weight ratio of 70/30) (200 mg/100 cm$^2$), (2) Timing layer having 4.5 μm in dry thickness containing cellulose diacetate (acetylation degree 55%) (57 mg/100 cm$^2$), copolymer of styrene and maleic anhydride (1.0 mg/100 cm$^2$) and 5-(2-cyanoethylthio)-1-phenyltetrazole as the precursor for development inhibiting agent (3 mg/100 cm$^2$) and (3) Timing layer having 1.5 μm in dry thickness containing ter-copolymer of acrylic acid (in the weight ratio of 15/79/6) (21 mg/100 cm$^2$).

The Elements 4-1 and 4-2 thus prepared were subjected to exposure according to the following processes d to g and then processed in a similar manner as in Example 1 after being combined with the above processing sheet and the alkaline processing composition-containing pods as used in Example 1:

Process d

A similar process for exposure as in Example 1.

Process e

[Exposure is made in the order of (e-1), (e-2) and (e-3).]

(e-1): Overall uniform exposure on the whole surface through the red interference filter (KL-65) so as to achieve the red density of 0.3.

(e-2): Overall uniform exposure on the whole surface through the green filter (KL-55) so as to achieve the green density of 0.3.

(e-3): The same imagewise exposure as in the process d.

Process f

[Exposure is made in the order of (f-1), (f-2) and (f-3).]

(f-1): The same exposure as (f-1) in the process e.

(f-2): The same exposure as (e-2) in the process e, except that, in place of the green filter, a blue filter ($\lambda_{max}$=436 nm, KL-44: manufactured by Tokyo Shibaura Denki) was used so as to achieve the blue density of 0.3.

(f-3): The same exposure as (e-3) in the process e.

Process g

[Exposure is made in the order of (g-1), (g-2) and (g-3).]

(g-1): Overall uniform exposure on the whole surface through the green interference filter (KL-65) so as to achieve the green density of 0.3.

(g-2): The same exposure as (f-2) in the process f.

(g-3): The same exposure as (e-3) in the process e.

The elements which had been subjected to exposure and the subsequent processing were estimated in a similar manner as in Example 3. Thus, the characteristic curves were obtained from the samples treated according to the process d and the tri-chromatic coefficients (α) were obtained from the samples treated according to the processes e to g in order to estimate the degree of color separation, wherein the color mixing of green density against blue density (process e; $D^G/D^B$) was represented by $\alpha^Y$ and the color mixing of blue density and red density against green density (process f; $D^B/D^G$ and $D^R/D^G$, respectively) was represented by $\alpha_B{}^M$ and $\alpha_R{}^M$, respectively and further the color mixing of green density against red density (process g; $D^G/D^R$) was represented by $\alpha^C$. Results obtained are summarized in Table 4.

From Table 4, it will be apparent that the sample containing hydroquinone compounds according to the present invention as compared with the comparison compounds have excellent properties with respect to minimum density ($D_{min}$), and improvement of the color separation without causing any fall of the maximum density ($D_{max}$).

TABLE 4

| Process for exposure | Compound | Sample No. 4-1 Comparative tri chromatic Comparison | 4-2 Present invention tri chromatic Hydroquinone compound according to this invention | 4-3 | 4-4 | 4-5 Blank monochromatic |
|---|---|---|---|---|---|---|
| Process d | B | 1.70 | 1.71 | — | — | 1.82 |
|  | $D_{max}$G | 1.83 | 1.82 | — | 1.95 | — |
|  | R | 1.98 | 1.95 | 2.10 | — | — |
|  | B | 0.27 | 0.21 | — | — | 0.24 |
|  | $D_{min}$G | 0.35 | 0.25 | — | 0.27 | — |
|  | R | 0.34 | 0.26 | 0.28 | — | — |
| Process e | $\alpha^Y$ | 0.03 | 0.00 | — | — | 0.01 |
|  | $\alpha_B{}^M$ | 0.30 | 0.02 | — | 0.04 | — |
| Process f | $\alpha_R{}^M$ | 0.03 | 0.00 | — | 0.01 | — |
| Process g | $\alpha^C$ | 0.05 | 0.02 | 0.02 | — | — |

EXAMPLE 5

On a paper support of which both surfaces have been laminated with polyethylene the following layers were coated successively to prepare a multi-color photographic paper sample 5-1 as a control light-sensitive material:

Sample 5-1 Control light-sensitive material (1) Red sensitive silver halide mulsion layer containing red sensitive negative type silver iodobromide emulsion (1.1 mol % of silver iodide, 7.6 mg/100 cm$^2$, calculated in terms of silver), cyan coupler F (3.0 mg/100 cm$^2$), dibutyl phthalate (1.5 mg/100 cm$^2$) and gelatin (30 mg/100 cm$^2$), (2) Inter-layer containing gelatin (18 mg/100 cm$^2$), (3) Green sensitive silver halide emulsion layer containing green sensitive negative type silver iodobromide emulsion (1.9 mol % of silver iodide, 6.8 mg/100 cm$^2$ calculated in terms of silver), magenta coupler G (4.0 mg/100 cm$^2$), dibutyl phthalate (2.0 mg/100 cm$^2$) and gelatin (28 mg/100 cm$^2$), (4) Yellow filter layer containing yellow colloidal silver (1.3 mg/100 cm$^2$) and gelatin (18 mg/100 cm$^2$), (5) Blue-sensitive silver halide emulsion layer containing blue sensitive negative type silver iodobromide emulsion (1.1 mg/100 cm$^2$ of silver iodide, 8.1 mg/100 cm$^2$, calculated in terms of silver), yellow coupler I (4.0 mg/100 cm$^2$), dibutyl phthalate (2.0 mg/100 cm$^2$) and gelatin (28 mg/100 cm$^2$) and (6) Protective layer containing 1,2-bis-vinyl-sulfonylethane (1.4 mg/100 cm$^2$) and gelatin (17 mg/100 cm$^2$).

In a similar manner light-sensitive materials according to this invention and for comparison were prepared as follows:

Sample 5-2 (Comparative)

This sample comprises the same structure as the sample 5-1, except that a comparison compound was added to each of the above layers of the sample 5-1. More specifically, to each of the layers (1), (3) and (5) was added the comparison compound I dissolved in dibutyl phthalate together with each coupler at an amount of 2% by weight of respective couplers. The amount of the coupler coated in this case was made equivalent to that in the sample 5-1. Further, to the layers (2), (4) and (6), the comparison compound I dissolved in dibutyl phthalate and dispersed in gelatin was added. The amount coated was 0.3 mg/100 cm$^2$.

Samples 5-3 to 5—5 (According to the present invention)

Three types of samples 5-3, 5-4 and 5—5 having the same structure as the sample 5-2, except that the comparison compound I in the sample 5-2 was replaced by the hydroquinone compounds (1), (15) and (16) respectively according to the present invention, was prepared. The amount of such hydroquinone compounds to be coated were made equimolar amount to the comparison compound in the above sample 5-2.

Five types of samples thus prepared were subjected to exposure in the same manner as d to g of Example 4, except that in the processes e to g, overall uniform exposure was adjusted so that the reflection density may be 0.2.

Then, these exposed samples were subjected to reversal color development process according to the following steps:

| Processing steps (23° C.) | Time |
|---|---|
| First development | 10 min. |
| Stopping | 2 min. |
| Washing with water | 5 min. |
| Color development | 10 min. |
| Stopping | 2 min. |
| Washing with water | 2 min. |
| Bleaching and fixing | 7 min. |
| Washing with water | 20 min. |
| Stabilization | 1 min. |

Compositions of the processing solutions used are as follows:

| First developing solution: | |
|---|---|
| Metol | 1 g |
| Anhydrous sodium sulfite | 100 g |
| Hydroquinone | 4 g |
| Anhydrous sodium carbonate | 27 g |
| Potassium bromide | 0.7 g |
| Potassium thiocyanate | 0.5 g |
| Water to make up 1.0 liter. | |
| Stopping solution: | |
| Nitrilotriacetic acid | 20 g |
| Potassium alum | 10 g |

| -continued | |
|---|---|
| Water to make up 1.0 liter. | |
| Color developing solution: | |
| Sodium chloride | 0.6 g |
| Sodium bromide | 0.4 g |
| Sodium hydroxide | 4.6 g |
| Diethylene glycol | 13.0 ml |
| Benzyl alcohol | 10.0 ml |
| Sodium tetraborate pentahydrate (Na$_2$B$_4$O$_7$ . 5H$_2$O) | 7.6 g |
| Sodium metaborate dihydrate (NaBO$_2$ . 2H$_2$O) | 1.7 g |
| Hydroxylamine ½ sulfate | 3.0 g |
| 4-Amino-3-methyl-N-ethyl-N-($\beta$-hydroxyethyl)-p-phenylenediamine sulfate | 4.5 g |
| Nitrilotriacetate | 2.5 g |
| Water to make up 1.0 liter. | |
| Bleaching and fixing solution: | |
| Ethylenediaminetetraacetic acid disodium salt | 5.6 g |
| Ethylenediaminetetraacetic acid iron sodium salt | 44 g |
| Boric acid | 32 g |
| Sodium tetraborate pentahydrate | 10.4 g |
| Ammonium thiosulfate | 112 g |
| Sodium thiosulfate pentahydrate | 22.4 g |
| Anhydrous sodium sulfite | 7.2 g |
| Water to make up 1.0 liter. | |
| Stabilizing solution: | |
| Hakkol (manufactured by Showa Kagaku-Kogyo) | 3 g |
| Formalin (28% aqueous solution) | 15 ml |
| Koniducks (manufactured by Konishiroku Photo Industry) | 7.5 ml |
| Sodium citrate | 1.0 g |
| Water to make up 1.0 liter. | |

Each of the samples thus color developed was evaluated in the same manner as in Example 4. Results obtained are shown in Table 5.

As apparent from Table 5, the samples containing the hydroquinone compounds according to this invention (Samples 5-3, 5-4 and 5-5) are noted to be more excellent as compared with not only the control sample (Sample 5-1) but also the samples containing the comparison compound (Sample 5-2) with the view that the color stain is satisfactorily inhibited and good color separation is achievable.

TABLE 5

| | | Sample No. | | | | |
|---|---|---|---|---|---|---|
| | | | 5-2 | 5-3 | 5-4 | 5-5 |
| | | | Comparison | Compound according to this invention | | |
| Process for exposure | Compound | 5-1 None | compound I | (1) | (15) | (16) |
| Process d | D$_{max}$ B | 2.36 | 2.30 | 2.31 | 2.32 | 2.30 |
| | D$_{max}$ G | 2.21 | 2.20 | 2.19 | 2.18 | 2.20 |
| | D$_{max}$ R | 2.15 | 2.14 | 2.15 | 2.16 | 2.14 |
| | D$_{min}$ B | 0.20 | 0.17 | 0.14 | 0.14 | 0.15 |
| | D$_{min}$ G | 0.19 | 0.17 | 0.12 | 0.13 | 0.12 |
| | D$_{min}$ R | 0.19 | 0.16 | 0.12 | 0.12 | 0.13 |
| Process e | $\alpha^Y$ | 0.15 | 0.12 | 0.09 | 0.10 | 0.09 |
| Process f | $\alpha_B^M$ | 0.36 | 0.32 | 0.27 | 0.26 | 0.28 |
| | $\alpha_R^M$ | 0.43 | 0.18 | 0.12 | 0.12 | 0.13 |
| Process g | $\alpha^C$ | 0.31 | 0.29 | 0.24 | 0.25 | 0.23 |

The comparison compounds, DRR compounds, DDR couplers used in these Examples 1 to 5 are listed below.

Comparison compound I

Comparison compound II

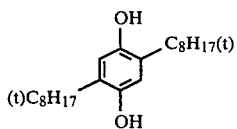
Comparison compound III
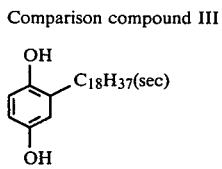
Comparison compound V
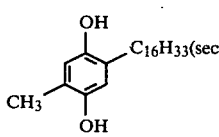
Cyan DDR coupler B
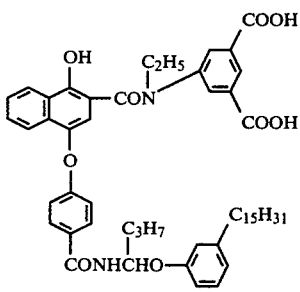
Cyan DDR compound D
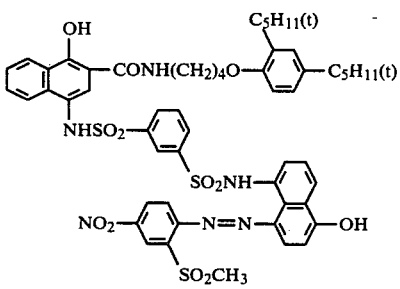
Cyan coupler F
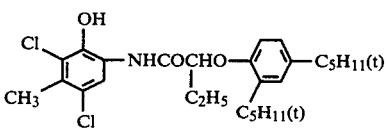
Yellow coupler I
-continued
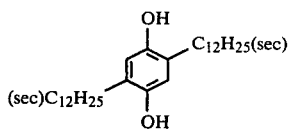
Comparison compound IV
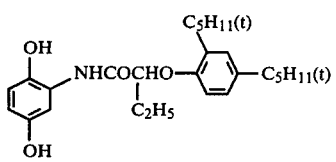
Magenta DRR compound A
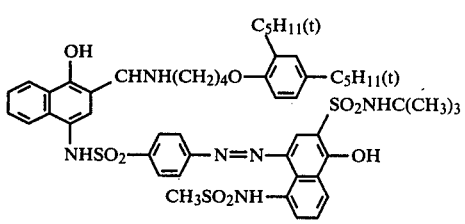
Magenta DDR coupler C
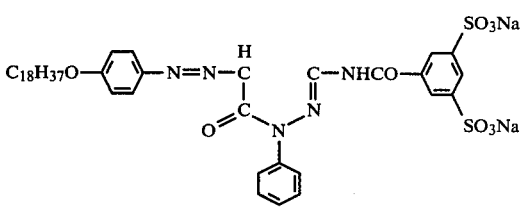
Yellow DRR compound E
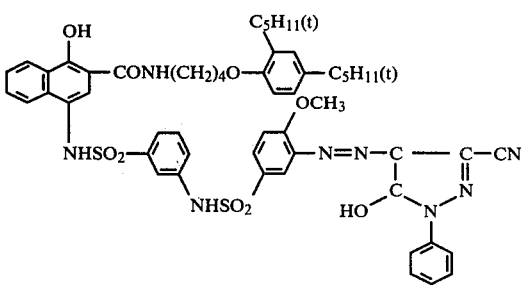
Magenta coupler G
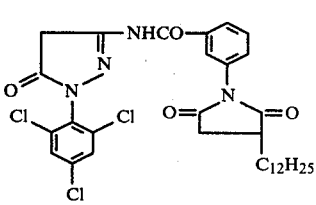
Optical whitening agent -continued

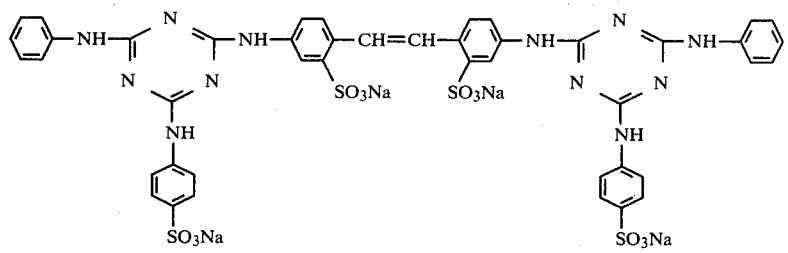

We claim:

1. A light sensitive color photographic material comprising a support and at least one hydrophilic colloid layer coated thereon which comprises a light-sensitive silver halide emulsion and an image dye-forming substance associated with said silver halide emulsion and, as a color fog inhibiting agent, a compound of the formula

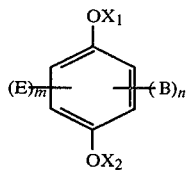

wherein E is nitro, cyano, formyl, trihalogenomethyl, $COR_7$, or $SO_2R_8$, wherein $R_7$ is alkyl and $R_8$ is aryl, B is halogen, alkyl, aryl, alkoxy, alkenyl, cycloalkyl, aryloxy, carbamoyl, amido, or sulfamoyl, $X_1$ and $X_2$ are individually hydrogen or a group which is capable of being split off under alkaline conditions, m and n are 1–3, provided that at least one B is alkyl having 8–36 carbon atoms and m+n=2–4.

2. The material of claim 1 wherein B is halogen, unsubstituted alkyl, aryl, alkoxy, alkenyl, cycloalkyl, aryloxy, carbamoyl, amido, or sulfamoyl.

3. The material of claim 2, wherein $R_7$ is alkyl having 1–3 carbon atoms.

4. The material of claim 2, wherein $X_1$ and $X_2$ independently are hydrogen or a group represented by the following formulas

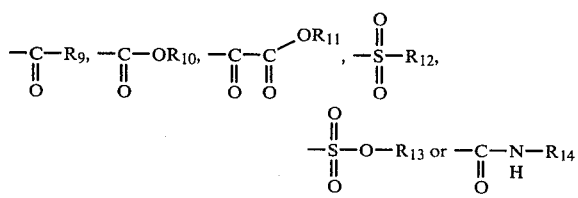

wherein $R_9$, $R_{10}$, $R_{11}$, $R_{12}$, $R_{13}$, and $R_{14}$ independently represent alkyl, cycloalkyl, alkenyl or aryl.

5. The material of claim 3 wherein E is $COR_7$, $R_7$ is methyl, ethyl, or propyl, and n is 1 or 2.

6. The material of claim 5 wherein $R_7$ is methyl.

7. The material of claim 2 wherein E is nitro or cyano and n is 1 or 2.

8. A light-sensitive color photographic material according to claim 2 wherein B is a branched alkyl group.

9. A light-sensitive color photographic material according to claim 2 wherein B is a secondary alkyl group.

10. A light-sensitive color photographic material according to claim 9 wherein said secondary alkyl group has from 10 to 22 carbon atoms 11. A light-sensitive color photographic material according to claim 2 wherein said hydroquinone compound is 2-nitro-5-sec-octadecyl hydroquinone, 2-cyano-5-sec-octadecyl hydroquinone or 2-acetyl-3,6-di-sec-dodecyl hydroquinone.

12. A light-sensitive color photographic material according to claim 1 wherein said hydroquinone compound or precursor is incorporated in an image dye-forming substance containing layer or a layer adjacent thereto, said image dye-forming substance being made associate with said silver halide emulsion.

13. A light-sensitive color photographic material according to claim 12 wherein said image dye-forming material is a compound represented by the general formula

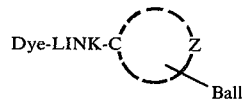

wherein DYE represents the residue of a diffusible dye or diffusible dye precursor, LINK represents —O—, —S—, —$SO_2$— or —$SO_2NH$— (where the nitrogen atom is attached to

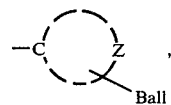

BALL represents a photographically inert ballast group having such size of molecule and/or conformation that enables to make the image dye-forming substance non-diffusible under alkaline condition and Z represents a non-metal atom group required for forming together with the carbon atom attached to said LINK, a 5- or 6-membered ring which can be split off from the LINK under alkaline condition upon the oxidation-reduction reaction with and oxidation product of a silver halide developing agent.

14. A light-sensitive color photographic material according to claim 2 wherein said material is a light-sensitive color photographic material suitable for forming a dye image by a redox reaction of an oxidation product of a 1-phenyl-3-pyrazolidone type developing agent.

15. A light-sensitive color photographic material according to claim 14 wherein said developing agent is 4-hydroxymethyl-4-methyl-1-phenyl-3-pyrazolidone.

16. A light-sensitive color photographic material according to claim 2 wherein said light-sensitive silver halide emulsion is a direct positive type emulsion having high internal sensitivity and low surface sensitivity.

17. A light-sensitive color photographic material according to claim 2 wherein said hydroquinone or precursor thereof is being incorporated into said material at a concentration ranging from $10^{-3}$ to $5\times10^{-1}$ moles per mole of silver halide.

18. A light-sensitive color photographic material according to claim 2 wherein said material is one suitable for a color diffusion transfer process.

* * * * *